(12) United States Patent
Keaney et al.

(10) Patent No.: US 11,767,319 B2
(45) Date of Patent: Sep. 26, 2023

(54) CRYSTALLINE FORMS OF A SELECTIVE C-KIT KINASE INHIBITOR

(71) Applicant: Third Harmonic Bio, Inc., Cambridge, MA (US)

(72) Inventors: Gregg F. Keaney, Lexington, MA (US); Leonard Walter Rozamus, Jr., Andover, MA (US); Jonathan James Loughrey, Edinburgh (GB); Jaclyn Raeburn, Glasgow (GB); Yuxiang Song, Suzhou (CN)

(73) Assignee: Third Harmonic Bio, Inc., Cambridge, MA (US)

( * ) Notice: Subject to any disclaimer, the term of this patent is extended or adjusted under 35 U.S.C. 154(b) by 0 days.

(21) Appl. No.: 17/305,862

(22) Filed: Jul. 15, 2021

(65) Prior Publication Data
US 2022/0056026 A1    Feb. 24, 2022

(30) Foreign Application Priority Data
Jul. 15, 2020   (WO) ............... PCT/CN2020/102095

(51) Int. Cl.
*C07D 471/04*   (2006.01)

(52) U.S. Cl.
CPC ........ *C07D 471/04* (2013.01); *C07B 2200/13* (2013.01)

(58) Field of Classification Search
CPC .................................................. C07D 471/04
USPC ......................................................... 514/300
See application file for complete search history.

(56) References Cited

U.S. PATENT DOCUMENTS

| | | | |
|---|---|---|---|
| 8,569,283 B2 | 10/2013 | Molteni et al. | |
| 8,569,583 B2 | 10/2013 | Donovan et al. | |
| 8,754,071 B2 | 6/2014 | Molenti et al. | |
| 9,023,839 B2 | 5/2015 | Molteni et al. | |
| 9,199,981 B2 * | 12/2015 | Yeh ...................... | A61P 11/04 |
| 2007/0072862 A1 | 3/2007 | Dimauro et al. | |
| 2013/0023751 A1 | 1/2013 | Lichtenstein et al. | |
| 2013/0059832 A1 | 3/2013 | Molteni et al. | |
| 2013/0059846 A1 | 3/2013 | Yeh et al. | |
| 2014/0228347 A1 | 8/2014 | Molteni et al. | |
| 2015/0011508 A1 | 1/2015 | Liu et al. | |
| 2015/0051206 A1 | 2/2015 | Loren et al. | |
| 2022/0056026 A1 | 2/2022 | Keaney et al. | |
| 2022/0184045 A1 | 6/2022 | Keaney et al. | |
| 2022/0194936 A1 | 6/2022 | Wang et al. | |

FOREIGN PATENT DOCUMENTS

| | | | |
|---|---|---|---|
| WO | 2006027795 A1 | 3/2006 | |
| WO | 2006071940 A2 | 7/2006 | |
| WO | 2007022380 A2 | 2/2007 | |
| WO | 2008058037 A1 | 5/2008 | |
| WO | WO-2011113606 A1 | 9/2011 | |
| WO | WO-2012143796 A2 | 10/2012 | |
| WO | 2013033070 A1 | 3/2013 | |
| WO | 2013033116 A1 | 3/2013 | |
| WO | 2013033167 A1 | 3/2013 | |
| WO | 2013033203 A1 | 3/2013 | |
| WO | 2013033620 A1 | 3/2013 | |
| WO | WO-2018140796 A1 | 8/2018 | |
| WO | 2020228746 | * | 5/2020 |
| WO | 2020228746 A1 | 11/2020 | |
| WO | WO-2022016021 A1 | 1/2022 | |

OTHER PUBLICATIONS

Babaei et al., "Receptor tyrosine kinase (c-Kit) inhibitors: a potential therapeutic target in cancer cells," Drug Des Devel Ther. 2016; 10:2443-59.

Database Registry, Chemical Abstracts Service, Columbus, Ohio, US, Apr. 14, 2011, XP002685983, Database accession No. 1280077-39-5, N-[3-(3-cycolopropyl-1H-1,2,4-triazol-5-yl)phenyl]-5-methylimidazo[1,2-a]pyridine-2-carboxamide.

Database Registry, Chemical Abstracts Service, Columbus, Ohio, US, Mar. 14, 2010, XP002685990, Database accession No. 1209616-10-3, N-[3-[6-[(4-morpholinyl)-3-pyridazinyl]phenyl-2-methylimidazo[1,2-a]pyridine-3-carboxamide.

International Search Report and Written Opinion issued by the European Patent Office, as International Searching Authority, for International Patent Application No. PCT/US2012/052621, dated Nov. 13, 2012 (10 pages).

International Search Report and Written Opinion issued by the European Patent Office, as International Searching Authority, for International Patent Application No. PCT/US2012/052802, dated Nov. 8, 2012 (10 pages).

International Search Report and Written Opinion issued by the National Intellectual Property Administration, PRC, as International, Searching Authority for International Patent Application No. PCT/CN2019/086582, dated Jan. 23, 2020 (15 pages).

International Search Report and Written Opinion issued by the National Intellectual Property Administration, PRC, as International, Searching Authority for International Patent Application No. PCT/CN2020/090060, dated Aug. 12, 2020 (14 pages).

International Search Report and Written Opinion issued by the National Intellectual Property Administration, PRC, as International, Searching Authority for International Patent Application No. PCT/CN2020/102095, dated Apr. 16, 2021 (18 pages).

(Continued)

*Primary Examiner* — Niloofar Rahmani

(74) *Attorney, Agent, or Firm* — Dechert LLP; Andrea L. C. Reid; Chad E. Davis

(57) ABSTRACT

The present disclosure relates generally to various forms and compositions of N-(5-(5-((1R,2S)-2-fluorocyclopropyl)-1,2,4-oxadiazol-3-yl)-2-methylphenyl)imidazo[1,2-a]pyridine-3-carboxamide useful as a selective inhibitor of c-kit kinase and uses of the same in the treatment of c-kit kinase associated diseases.

24 Claims, 19 Drawing Sheets

(56) References Cited

OTHER PUBLICATIONS

International Search Report and Written Opinion issued by the United States Patent and Trademark Office as International Searching Authority for International Patent Application No. PCT/US2021/041903, dated Oct. 28, 2021 (9 pages).
Pubchem, N-(5-(5-((1R,2S)-2-Fluorocyclopropyl)-1 2,4-oxadiazol-3-yl)-2-methylphenyl)imidazo[1,2-a]pyridine-3-carboxamide, CID 71280305, Mar. 21, 2013, modified Sep. 25, 2021 (13 pages). Available at: https://pubchem.ncbi.nlm.gov/compound/71280305.
Pubchem, N-[5-[5-(2-Fluorocyclopropyl)-1,2,4-oxadiazol-3-yl]-2-methylphenyl]imidazo[1 2-a]pyridine-3-carboxamide, CID 78048019, Sep. 25, 2014, modified Sep. 25, 2021 (8 pages). Available at: https://pubchem.ncbi.nlm.gov/compound/78048019.
Roskoski, "The role of small molecule Kit protein-tyrosine kinase inhibitors in the treatment of neoplastic disorders," Pharmacol Res. 2018; 133:35-52.
Database Registry, Chemical Abstracts Service, Columbus, Ohio, US, Mar. 14, 2010, XP002685990, Database accession No. 1209616-10-3, N-[346-[(4-morpholinyl)-3-pyridazinyl]phenyl-2-methylimidazo[1,2-a]pyridine-3-carboxamide.
Morphy, "Selectively Nonselective Kinase Inhibition: Striking the Right Balance," J Med Chem. 2010;53(4).
Kim et al., "Design and Synthesis of Imidazopyridine Analogues as Inhibitors of Phosphoinositide 3-Kinase Signaling and Angiogenesis," J Med Chem. 2011;54(7).
Caira, M.R., "Crystalline Polymorphism of Organic Compounds." Design of Organic Solids. Topics in Current Chemistry. 1998:198;163-208.
Pecharsky and Zavalij, "Fundamentals of Powder Diffraction and Structural Charaterization of Materials," Kluwer Academic Publishers. 2003;3.
U.S. Department of Health and Human Services et al., "Regulatory Classification of Pharmaceutical Co-Crystals: Guidance for Industry.," Draft Guidance. 2016;Revision 1.
PCT International Search Report and Written Opinion from PCT/EP2021/082295 dated Feb. 23, 2022.
PCT International Search Report and Written Opinion from PCT/US2021/072503 dated Feb. 16, 2022.

\* cited by examiner

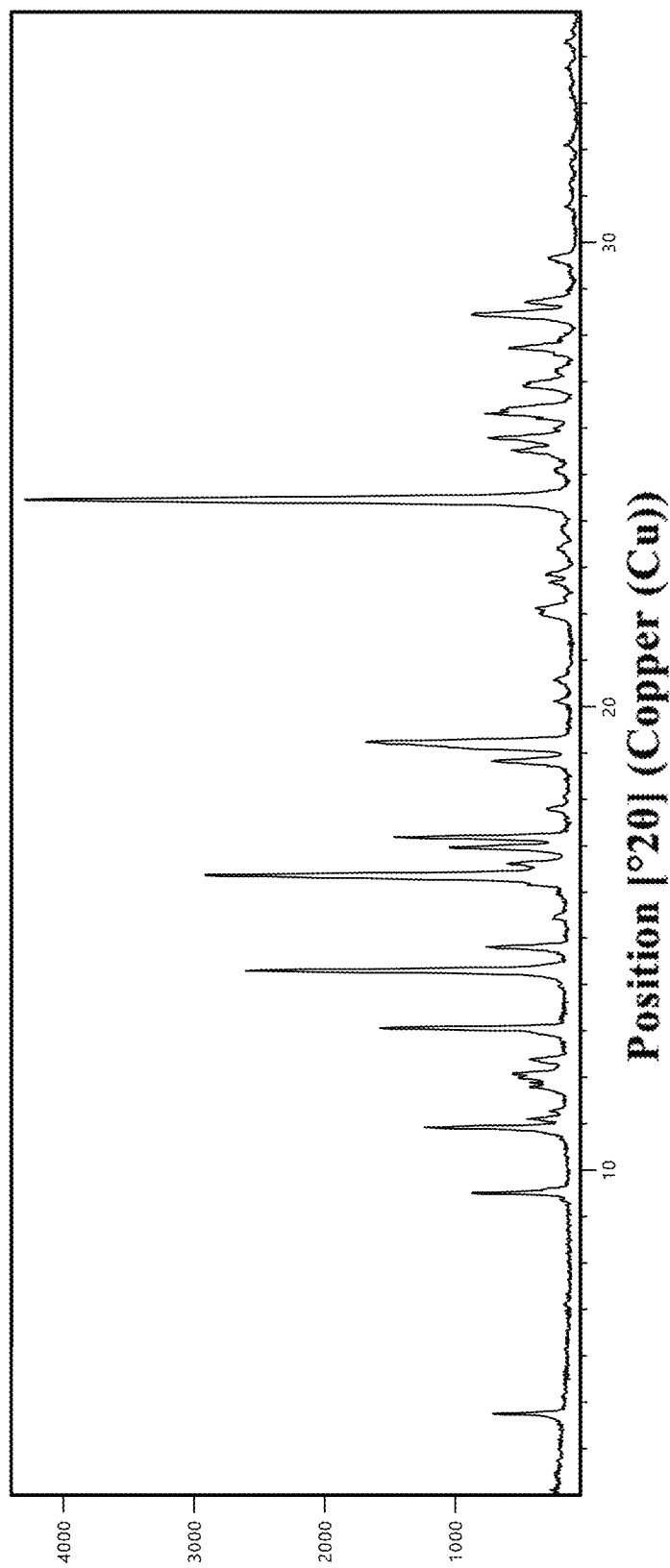

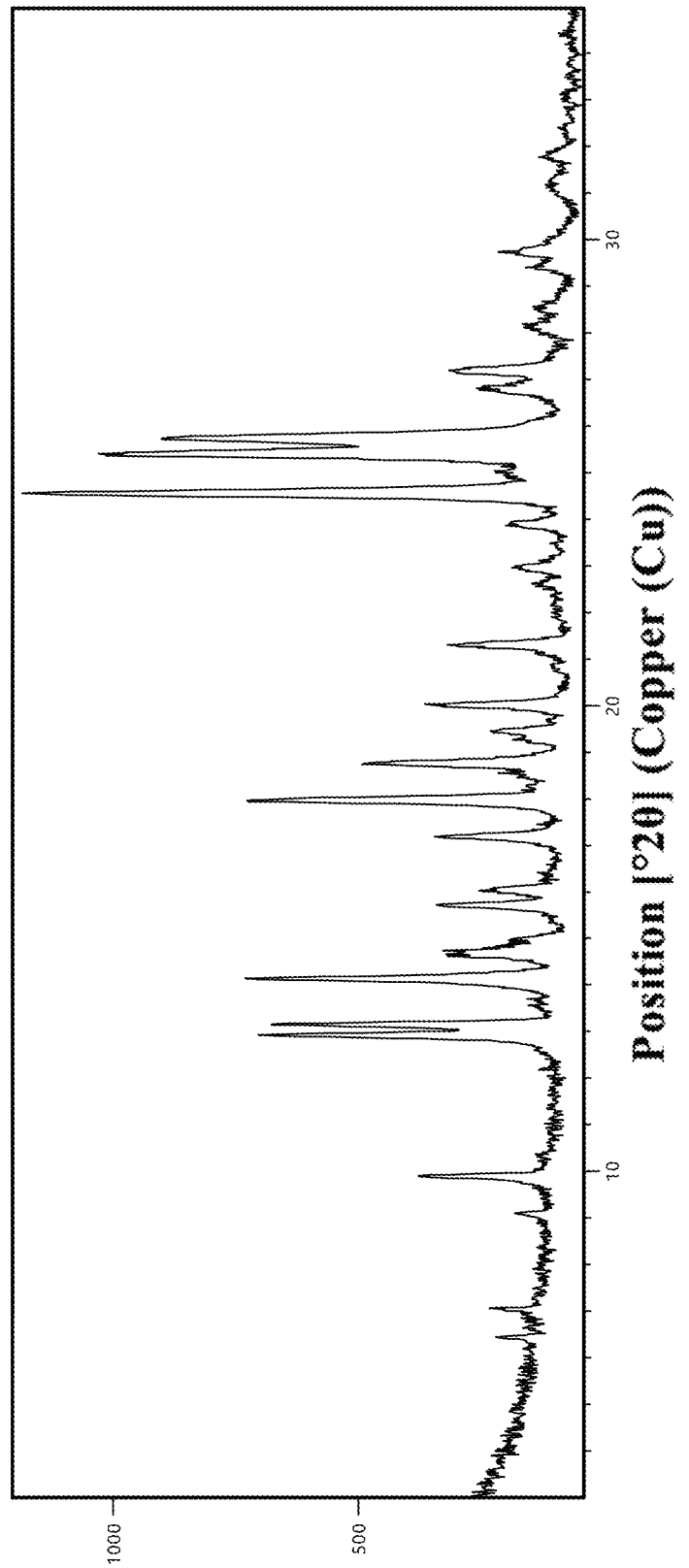

CRYSTALLINE FORMS OF A SELECTIVE C-KIT KINASE INHIBITOR

CROSS REFERENCE TO RELATED APPLICATION

This application claims the benefit of PCT Application PCT/CN2020/102095, filed Jul. 15, 2020, the entirety of which is incorporated herein by reference.

FIELD OF THE INVENTION

The present disclosure relates generally to various forms and compositions of N-(5-(5-((1R,2S)-2-fluorocyclopropyl)-1,2,4-oxadiazol-3-yl)-2-methylphenyl)imidazo[1,2-a]pyridine-3-carboxamide useful as a selective inhibitor of c-kit kinase and uses of the same in the treatment of c-kit kinase associated diseases.

BACKGROUND

N-(5-(5-((1R,2S)-2-fluorocyclopropyl)-1,2,4-oxadiazol-3-yl)-2-methylphenyl)imidazo[1,2-a]pyridine-3-carboxamide, first disclosed in WO 2013/033070 A1, is a selective inhibitor of c-kit kinase, useful for the depletion of mast cells and thus is useful for treating mast-cell associated diseases including asthma, allergic rhinitis, pulmonary arterial hypertension (PAH), pulmonary fibrosis, hepatic fibrosis, cardiac fibrosis, scleroderma, irritable bowel syndrome (IBS), inflammatory bowel disease (IBD), urticaria, dermatosis, atopic dermatitis, allergic contact dermatitis, rheumatoid arthritis, multiple sclerosis, melanoma, a gastrointestinal stromal tumor, a mast cell tumor, mastocytosis, anaphylactic syndrome, food allergy, type I diabetes and type II diabetes.

There remains a need in the art for novel compounds, chemical forms, compositions and methods for treating mast-cell associated diseases.

SUMMARY OF THE INVENTION

It has now been found that novel forms of the present disclosure, and compositions thereof, are useful as selective inhibitor of c-kit kinase and exhibit desirable characteristics for the same. In general, salt forms or freebase forms, and pharmaceutically acceptable compositions thereof, are useful for treating or lessening the severity of a variety of diseases or disorders as described in detail herein.

BRIEF DESCRIPTION OF THE DRAWINGS

FIG. 3A depicts an XRPD pattern of Form E of compound 1.

FIG. 5A depicts an XRPD pattern of Form H of compound 1.

DETAILED DESCRIPTION OF THE INVENTION

Figure 1A:
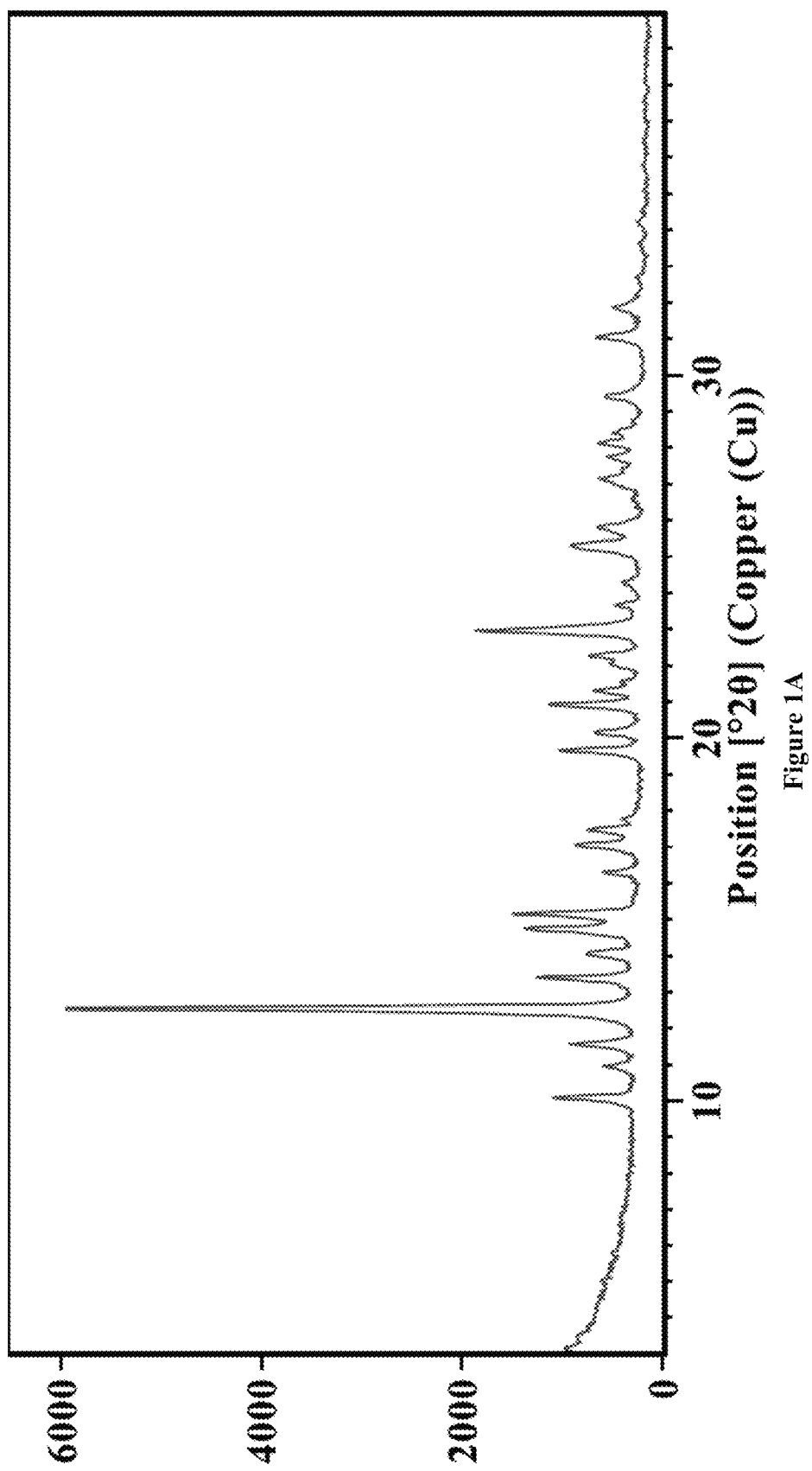
FIG. 1A depicts an XRPD pattern of Form C of compound 1.

General Description of Certain Aspects of the Invention

The present disclosure is based at least in part on the identification of a compound that modulates c-kit kinase and methods of using the same to treat c-kit kinase associated diseases. Disclosed herein is compound 1, and salts and solid forms thereof:

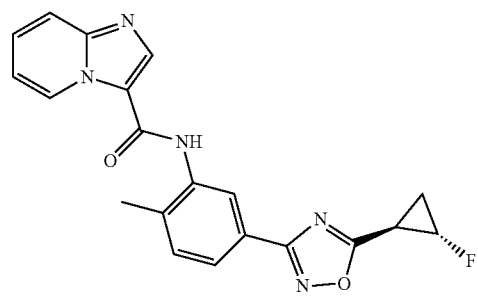

Compound 1, N-(5-(5-((1R,2S)-2-fluorocyclopropyl)-1,2,4-oxadiazol-3-yl)-2-methylphenyl)imidazo[1,2-a]pyridine-3-carboxamide, is active in a variety of assays and therapeutic models, acting as a selective inhibitor of c-kit kinase.

It would be desirable to provide a solid form of compound 1 (e.g., as a freebase thereof or salt thereof) that imparts characteristics such as improved aqueous solubility, stability and ease of formulation. Accordingly, the present disclosure provides both free base forms and salt forms of compound 1.

Free Base Forms of Compound 1

It is contemplated that compound 1 can exist in a variety of physical forms. For example, compound 1 can be in solution, suspension, or in solid form. In certain embodiments, compound 1 is in solid form. When compound 1 is in solid form, said compound may be amorphous, crystalline, or a mixture thereof. Exemplary solid forms are described in more detail below.

In some embodiments, the present disclosure provides a form of compound 1 substantially free of impurities. As used herein, the term "substantially free of impurities" means that the compound contains no significant amount of extraneous matter. Such extraneous matter may include different forms of compound 1, residual solvents, or any other impurities that may result from the preparation of, and/or isolation of, compound 1. In certain embodiments, at least about 95% by weight of a form of compound 1 is present. In still other embodiments of the disclosure, at least about 99% by weight of a form of compound 1 is present.

According to one embodiment, a form of compound 1 is present in an amount of at least about 97, 97.5, 98.0, 98.5, 99, 99.5, 99.8 weight percent where the percentages are based on the total weight of the composition. According to another embodiment, a form of compound 1 contains no more than about 3.0 area percent HPLC of total organic impurities and, in certain embodiments, no more than about 1.5 area percent HPLC total organic impurities relative to the total area of the HPLC chromatogram. In other embodiments, a form of compound 1 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for a form of compound 1 is also meant to include all tautomeric forms of compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this disclosure.

It has been found that compound 1 can exist in a variety of solid forms. Exemplary such forms include polymorphs such as those described herein.

As used herein, the term "polymorph" refers to the different crystal structures into which a compound, or a salt or solvate thereof, can crystallize.

In certain embodiments, compound 1 is a crystalline solid. In other embodiments, compound 1 is a crystalline solid substantially free of amorphous compound 1. As used herein, the term "substantially free of amorphous compound 1" means that the compound contains no significant amount of amorphous compound 1. In certain embodiments, at least about 95% by weight of crystalline compound 1 is present. In still other embodiments of the disclosure, at least about 99% by weight of crystalline compound 1 is present.

It has been found that the free base compound 1 can exist in at least two distinct polymorphic forms. In certain embodiments, the present disclosure provides a polymorphic form of compound 1 referred to herein as Form C. In certain embodiments, the present disclosure provides a polymorphic form of compound 1 referred to herein as Form D. In certain embodiments, the present disclosure provides a polymorphic form of compound 1 referred to herein as Form E. In certain embodiments, the present disclosure provides a polymorphic form of compound 1 referred to herein as Form G. In certain embodiments, the present disclosure provides a polymorphic form of compound 1 referred to herein as Form H.

In some embodiments, compound 1 is amorphous. In some embodiments, compound 1 is amorphous, and is substantially free of crystalline compound 1.

Form C of Compound 1

In some embodiments, Form C of compound 1 is a form having at least 1, 2, 3, 4 or 5 spectral peak(s) selected from the peaks listed in Table 1 below.

TABLE 1

XRPD Peak Positions for Form C of Compound 1

| Position (°2θ) | Intensity % |
|---|---|
| 3.2 | 4.6 |
| 10.1 | 12.8 |
| 10.9 | 5.0 |
| 11.6 | 10.4 |
| 12.5 | 100.0 |
| 13.4 | 15.8 |
| 14.1 | 7.9 |
| 14.7 | 18.1 |
| 15.2 | 20.0 |
| 16.3 | 5.2 |
| 17.0 | 10.3 |
| 17.5 | 7.9 |
| 17.8 | 2.7 |
| 19.7 | 13.1 |
| 20.1 | 7.3 |
| 20.9 | 14.6 |
| 21.3 | 7.6 |
| 22.0 | 4.7 |
| 22.3 | 8.4 |
| 23.0 | 26.7 |
| 23.7 | 4.4 |
| 24.3 | 2.7 |
| 25.3 | 11.4 |
| 25.8 | 7.3 |
| 27.1 | 7.2 |
| 27.8 | 5.8 |
| 28.1 | 6.5 |
| 28.5 | 4.4 |
| 29.4 | 6.0 |
| 31.0 | 7.6 |
| 31.9 | 5.2 |
| 32.7 | 1.5 |
| 33.6 | 0.8 |
| 34.2 | 1.7 |
| 36.1 | 0.1 |
| 37.2 | 0.1 |

In this and all subsequent tables, the position (°2θ) is within ±0.2.

In some embodiments, Form C of compound 1 is characterized in that it has one or more peaks in its X-ray powder diffraction pattern selected from those at about 10.1, about 12.5, about 15.2, about 19.7, about 20.9, about 23.0, and about 25.3 degrees 2-theta. In some embodiments, Form C of compound 1 is characterized in that it has two or more peaks in its X-ray powder diffraction pattern selected from those at about 10.1, about 12.5, about 15.2, about 19.7, about 20.9, about 23.0, and about 25.3 degrees 2-theta. In some embodiments, Form C of compound 1 is characterized in that it has three or more peaks in its X-ray powder diffraction pattern selected from those at about 10.1, about 12.5, about 15.2, about 19.7, about 20.9, about 23.0, and about 25.3 degrees 2-theta. In some embodiments, Form C of compound 1 is characterized in that it has four or more peaks in its X-ray powder diffraction pattern selected from those at about 10.1, about 12.5, about 15.2, about 19.7, about 20.9, about 23.0, and about 25.3 degrees 2-theta. In some embodiments, Form C of compound 1 is characterized in that it has five or more peaks in its X-ray powder diffraction pattern selected from those at about 10.1, about 12.5, about 15.2, about 19.7, about 20.9, about 23.0, and about 25.3 degrees 2-theta. In some embodiments, Form C of compound 1 is characterized in that it has six or more peaks in its X-ray powder diffraction pattern selected from those at about 10.1, about 12.5, about 15.2, about 19.7, about 20.9, about 23.0, and about 25.3 degrees 2-theta. In some embodiments, Form C of compound 1 is characterized in that it has seven peaks in its X-ray powder diffraction pattern selected from those at about 10.1, about 12.5, about 15.2, about 19.7, about 20.9, about 23.0, and about 25.3 degrees 2-theta. As used herein, the term "about", when used in reference to a degree 2-theta value refers to the stated value ±0.2 degree 2-theta.

In some embodiments, Form C of compound 1 is characterized in that it has each of the spectral peaks in its X-ray powder diffraction pattern listed in Table 1 having a relative intensity greater than 10%, 20%, 30% or 40%. In certain embodiments, the X-ray powder diffraction pattern is substantially similar to the XRPD provided in FIG. 1A.

Methods for preparing Form C of compound 1 are described infra.

In some embodiments, Form C is a hydrate form of compound 1. In some embodiments, Form C is a dihydrate form of compound 1.

Form D of Compound 1

In some embodiments, Form D of compound 1 is a form having at least 1, 2, 3, 4 or 5 spectral peak(s) selected from the peaks listed in Table 2 below.

TABLE 2

XRPD Peak Positions for
Form D of Compound 1

| Position (°2θ) | Intensity % |
|---|---|
| 3.1 | 14.1 |
| 5.1 | 8.8 |
| 8.9 | 34.7 |
| 9.9 | 80.7 |
| 10.2 | 9.5 |
| 11.4 | 4.8 |
| 13.3 | 71.7 |
| 15.3 | 46.3 |
| 17.2 | 90.7 |
| 17.7 | 61.8 |
| 18.6 | 28.2 |
| 19.8 | 100.0 |
| 20.4 | 10.6 |
| 21.3 | 2.5 |
| 22.1 | 17.2 |
| 22.9 | 10.8 |
| 24.6 | 3.9 |
| 26.1 | 28.0 |
| 26.9 | 4.2 |
| 27.6 | 5.1 |
| 27.9 | 2.5 |
| 29.9 | 2.4 |
| 31.4 | 2.2 |
| 32.0 | 0.8 |
| 33.0 | 1.5 |
| 34.3 | 2.0 |
| 34.7 | 2.0 |

In this and all subsequent tables, the position (°2θ) is within ±0.2.

In some embodiments, Form D of compound 1 is characterized in that it has one or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of compound 1 is characterized in that it has two or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of compound 1 is characterized in that it has three or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of compound 1 is characterized in that it has four or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of compound 1 is characterized in that it has five or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of compound 1 is characterized in that it has six or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of compound 1 is characterized in that it has seven or more peaks in its X-ray powder diffraction pattern selected from those at about 8.9, about 9.9, about 13.3, about 15.3, about 17.2, about 17.7, about 19.8, about 26.1 degrees 2-theta. In some embodiments, Form D of compound 1 is characterized in that it has eight peaks in its X-ray powder diffraction pattern at about 8.9, about 9.9, about 13.3, about 15.3, about 17.2, about 17.7, about 19.8, about 26.1 degrees 2-theta. In some embodiments, Form D of compound 1 is characterized in that it has each of the spectral peaks in its X-ray powder diffraction pattern listed in Table 2 having a relative intensity greater than 10%, 20%, 30% or 40%.

Figure 2A:
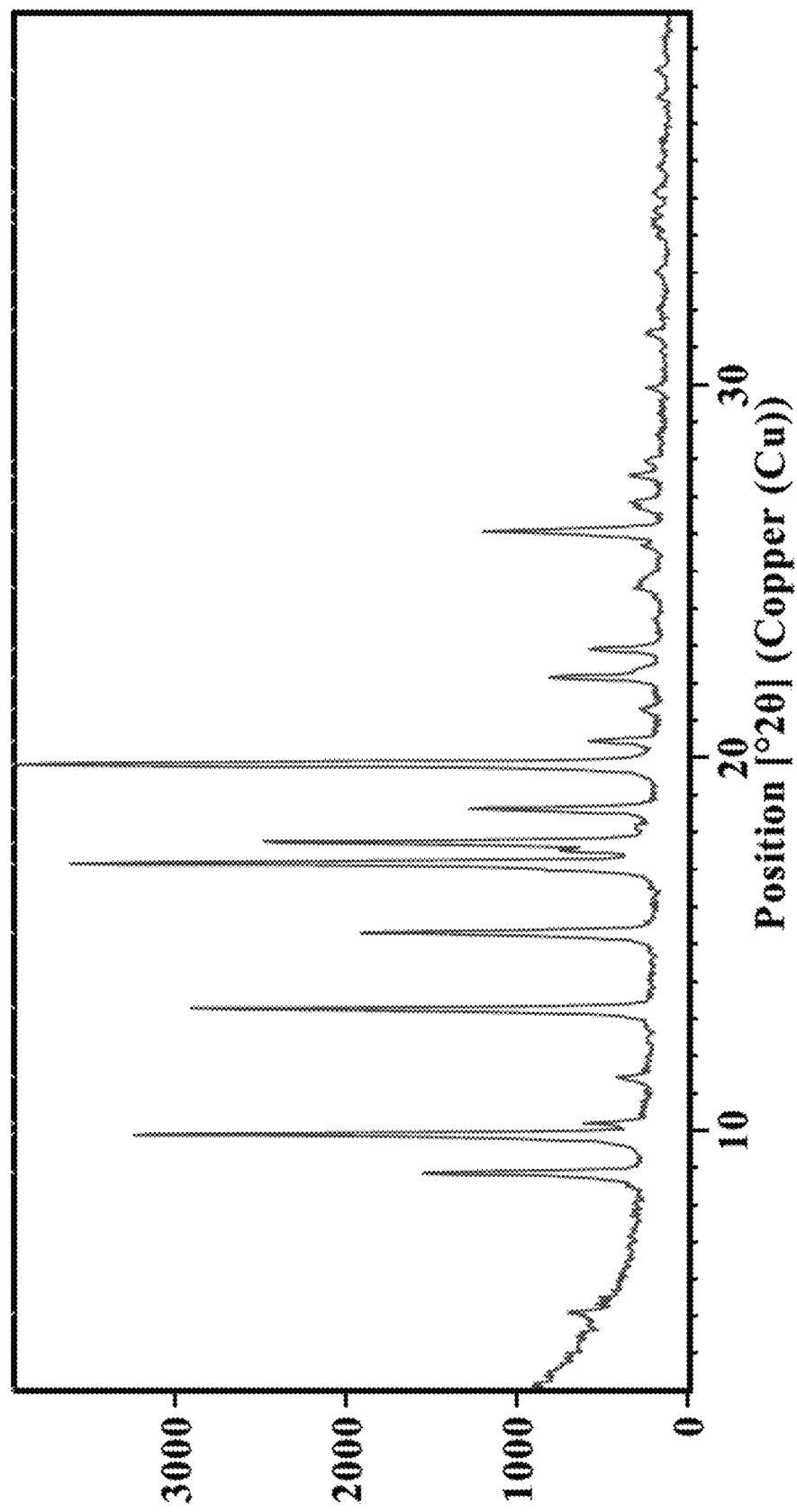
FIG. 2A depicts an XRPD pattern of Form D of compound 1.

In certain embodiments, the X-ray powder diffraction pattern is substantially similar to the XRPD provided in FIG. 2A.

Methods for preparing Form D of compound 1 are described infra.

In some embodiments, Form D is an anhydrate form of compound 1.

Form E of Compound 1

In some embodiments, Form E of compound 1 is an ethanol solvate form having at least 1, 2, 3, 4 or 5 spectral peak(s) selected from the peaks listed in Table 3 below.

TABLE 3

XRPD Peak Positions for
Form E of Compound 1

| Position (°2θ) | Intensity % |
|---|---|
| 4.8 | 12.9 |
| 9.5 | 17.6 |
| 10.9 | 25.4 |
| 13.1 | 33.8 |
| 14.3 | 58.3 |
| 14.8 | 14.3 |
| 16.4 | 65.6 |
| 16.6 | 9.5 |
| 17.0 | 20.9 |
| 17.2 | 31.2 |
| 18.8 | 13.9 |
| 19.1 | 17.7 |
| 19.2 | 36.1 |
| 24.5 | 100.0 |
| 25.5 | 9.4 |
| 25.8 | 14.0 |
| 26.3 | 14.4 |
| 26.4 | 10.2 |
| 27.7 | 11.3 |
| 28.4 | 17.5 |

In this and all subsequent tables, the position (°2θ) is within ±0.2.

In some embodiments, Form E of compound 1 is characterized in that it has one or more peaks in its X-ray powder diffraction pattern selected from those at about 13.1, about 14.3, about 16.4, about 17.2, about 19.2, and about 24.5 degrees 2-theta. In some embodiments, Form E of compound 1 is characterized in that it has two or more peaks in its X-ray powder diffraction pattern selected from those at about 13.1, about 14.3, about 16.4, about 17.2, about 19.2, and about 24.5 degrees 2-theta. In some embodiments, Form E of compound 1 is characterized in that it has three or more peaks in its X-ray powder diffraction pattern selected from those at about 13.1, about 14.3, about 16.4, about 17.2, about 19.2, and about 24.5 degrees 2-theta. In some embodiments, Form E of compound 1 is characterized in that it has four or more peaks in its X-ray powder diffraction pattern selected from those at about 13.1, about 14.3, about 16.4, about 17.2, about 19.2, and about 24.5 degrees 2-theta. In some embodiments, Form E of compound 1 is characterized in that it has five or more peaks in its X-ray powder diffraction pattern selected from those at about 13.1, about 14.3, about 16.4, about 17.2, about 19.2, and about 24.5 degrees 2-theta. In some embodiments, Form E of compound 1 is characterized in that it has six peaks in its X-ray powder diffraction pattern at about 13.1, about 14.3, about 16.4, about 17.2, about 19.2, and about 24.5 degrees 2-theta. In some embodiments, Form E of compound 1 is characterized in that it has each of the spectral peaks in its X-ray powder diffraction pattern listed in Table 3 having a relative intensity greater than 10%, 20%, 30% or 40%.

In certain embodiments, the X-ray powder diffraction pattern is substantially similar to the XRPD provided in FIG. 3A.

Methods for preparing Form E of compound 1 are described infra.

In some embodiments, Form E is an ethanol solvate form of compound 1.

Form G of Compound 1

In some embodiments, Form G of compound 1 is a form having at least 1, 2, 3, 4 or 5 spectral peak(s) selected from the peaks listed in Table 4 below.

TABLE 4

XRPD Peak Positions for Form G of Compound 1

| Position (°2θ) | Intensity % |
|---|---|
| 5.8 | 85.1 |
| 11.7 | 15.2 |
| 12.3 | 54.2 |
| 13.5 | 42.5 |
| 13.7 | 42.0 |
| 14.0 | 26.4 |
| 14.1 | 25.2 |
| 16.8 | 100.0 |
| 17.0 | 62.5 |
| 17.5 | 97.1 |
| 21.4 | 27.5 |
| 21.7 | 20.1 |
| 22.6 | 93.0 |
| 24.6 | 74.5 |
| 25.1 | 33.9 |
| 25.5 | 40.4 |
| 27.5 | 38.6 |
| 28.2 | 10.3 |
| 30.6 | 18.3 |
| 33.6 | 18.3 |

In this and all subsequent tables, the position (°2θ) is within ±0.2.

In some embodiments, Form G of compound 1 is characterized in that it has one or more peaks in its X-ray powder diffraction pattern selected from those at about 5.8, about 12.3, about 16.8, about 17.0, about 17.5, about 22.6, and about 24.6 degrees 2-theta. In some embodiments, Form G of compound 1 is characterized in that it has two or more peaks in its X-ray powder diffraction pattern selected from those at about 5.8, about 12.3, about 16.8, about 17.0, about 17.5, about 22.6, and about 24.6 degrees 2-theta. In some embodiments, Form G of compound 1 is characterized in that it has three or more peaks in its X-ray powder diffraction pattern selected from those at about 5.8, about 12.3, about 16.8, about 17.0, about 17.5, about 22.6, and about 24.6 degrees 2-theta. In some embodiments, Form G of compound 1 is characterized in that it has four or more peaks in its X-ray powder diffraction pattern selected from those at about 5.8, about 12.3, about 16.8, about 17.0, about 17.5, about 22.6, and about 24.6 degrees 2-theta. In some embodiments, Form G of compound 1 is characterized in that it has five or more peaks in its X-ray powder diffraction pattern selected from those at about 5.8, about 12.3, about 16.8, about 17.0, about 17.5, about 22.6, and about 24.6 degrees 2-theta. In some embodiments, Form G of compound 1 is characterized in that it has six or more peaks in its X-ray powder diffraction pattern at about 5.8, about 12.3, about 16.8, about 17.0, about 17.5, about 22.6, and about 24.6 degrees 2-theta. In some embodiments, Form G of compound 1 is characterized in that it has seven in its X-ray powder diffraction pattern at about 5.8, about 12.3, about 16.8, about 17.0, about 17.5, about 22.6, and about 24.6 degrees 2-theta. In some embodiments, Form G of compound 1 is characterized in that it has each of the spectral peaks in its X-ray powder diffraction pattern listed in Table 4 having a relative intensity greater than 10%, 20%, 30% or 40%.

Figure 4A:
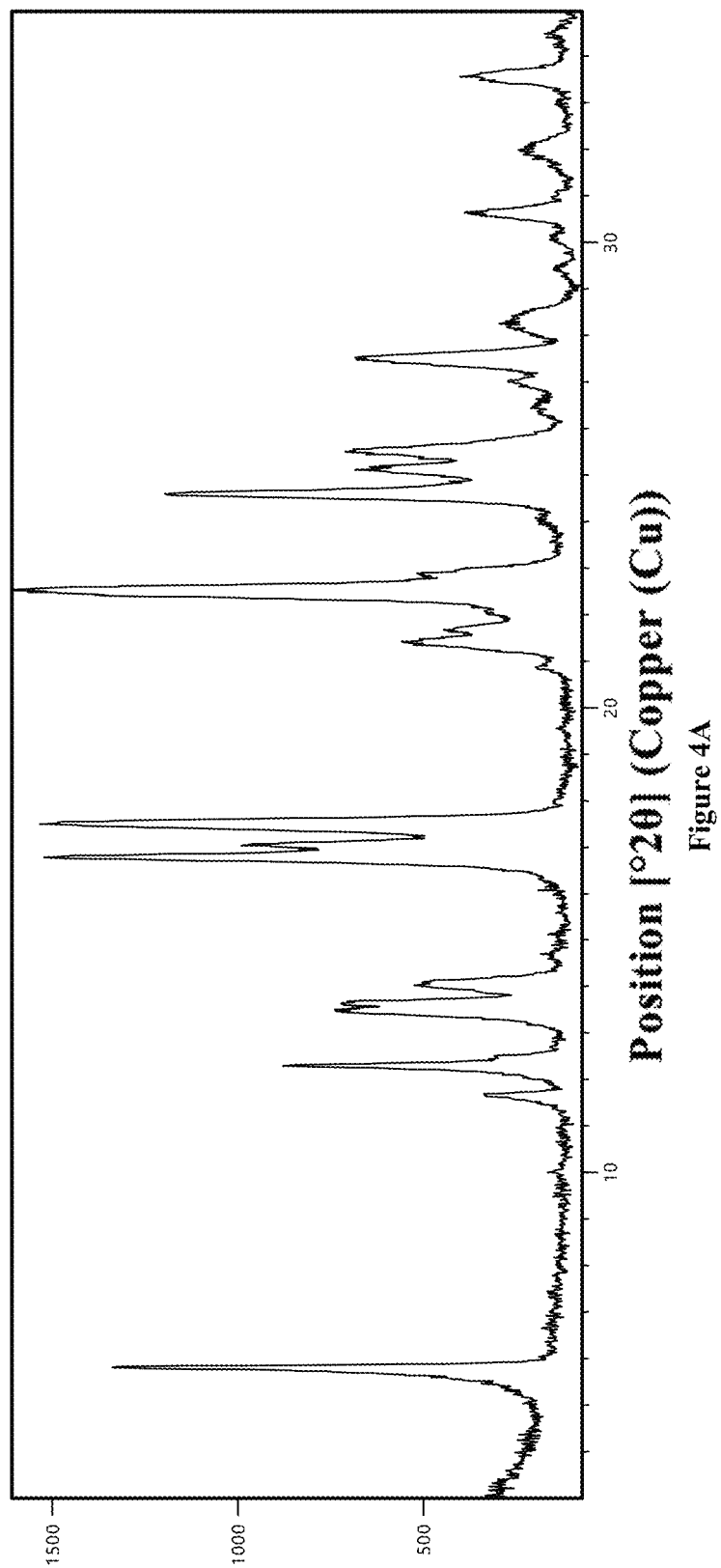
FIG. 4A depicts an XRPD pattern of Form G of compound 1.

In certain embodiments, the X-ray powder diffraction pattern is substantially similar to the XRPD provided in FIG. 4A.

Methods for preparing Form G of compound 1 are described infra.

In some embodiments, Form G is an anhydrate form. In some embodiments, Form G is a metastable anhydrate which readily hydrates to Form C of compound 1 under ambient conditions.

Form H of Compound 1

In some embodiments, Form H of compound 1 is a form having at least 1, 2, 3, 4 or 5 spectral peak(s) selected from the peaks listed in Table 5 below.

TABLE 5

XRPD Peak Positions for Form H of Compound 1

| Position (°2θ) | Intensity % |
|---|---|
| 7.1 | 10.1 |
| 9.9 | 23.1 |
| 12.9 | 56.9 |
| 13.2 | 53.3 |
| 14.1 | 58.9 |
| 14.6 | 18.5 |
| 15.7 | 21.8 |
| 16.1 | 13.0 |
| 17.2 | 23.3 |
| 17.9 | 59.7 |
| 18.8 | 36.2 |
| 19.4 | 11.7 |
| 20.0 | 23.7 |
| 21.3 | 22.7 |
| 24.6 | 100.0 |
| 25.4 | 73.1 |

TABLE 5-continued

XRPD Peak Positions for
Form H of Compound 1

| Position (°2θ) | Intensity % |
|---|---|
| 25.7 | 74.5 |
| 26.8 | 13.5 |
| 27.2 | 19.3 |
| 29.7 | 10.4 |

In this and all subsequent tables, the position (°2θ) is within ±0.2.

In some embodiments, Form H of compound 1 is characterized in that it has one or more peaks in its X-ray powder diffraction pattern selected from those at about 12.9, about 13.2, about 14.1, about 17.9, about 24.6, about 25.4, and about 25.7 degrees 2-theta. In some embodiments, Form H of compound 1 is characterized in that it has two or more peaks in its X-ray powder diffraction pattern selected from those at about 12.9, about 13.2, about 14.1, about 17.9, about 24.6, about 25.4, and about 25.7 degrees 2-theta. In some embodiments, Form H of compound 1 is characterized in that it has three or more peaks in its X-ray powder diffraction pattern selected from those at about 12.9, about 13.2, about 14.1, about 17.9, about 24.6, about 25.4, and about 25.7 degrees 2-theta. In some embodiments, Form H of compound 1 is characterized in that it has four or more peaks in its X-ray powder diffraction pattern selected from those at about 12.9, about 13.2, about 14.1, about 17.9, about 24.6, about 25.4, and about 25.7 degrees 2-theta. In some embodiments, Form H of compound 1 is characterized in that it has five or more peaks in its X-ray powder diffraction pattern selected from those at about 12.9, about 13.2, about 14.1, about 17.9, about 24.6, about 25.4, and about 25.7 degrees 2-theta. In some embodiments, Form H of compound 1 is characterized in that it has six or more peaks in its X-ray powder diffraction pattern at about 12.9, about 13.2, about 14.1, about 17.9, about 24.6, about 25.4, and about 25.7 degrees 2-theta. In some embodiments, Form H of compound 1 is characterized in that it has seven in its X-ray powder diffraction pattern at about 12.9, about 13.2, about 14.1, about 17.9, about 24.6, about 25.4, and about 25.7 degrees 2-theta. In some embodiments, Form H of compound 1 is characterized in that it has each of the spectral peaks in its X-ray powder diffraction pattern listed in Table 5 having a relative intensity greater than 10%, 20%, 30% or 40%.

In certain embodiments, the X-ray powder diffraction pattern is substantially similar to the XRPD provided in FIG. 5A.

Methods for preparing Form H of compound 1 are described infra.

In some embodiments, Form H is a hydrate, hemi-hydrate, methanol-solvate or methanol-solvate/hydrate form.

In some embodiments, the disclosure provides compound 1:

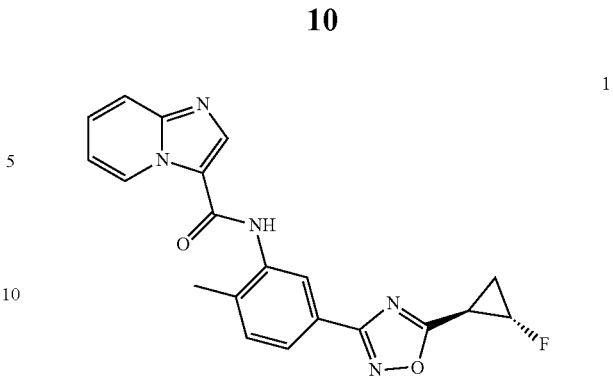

wherein said compound is crystalline. In some embodiments, the present disclosure provides compound 1, wherein said compound is substantially free of amorphous compound 1.

In some embodiments, the present disclosure provides compound 1, wherein said compound is substantially free of impurities.

In some embodiments, the present disclosure provides compound 1, wherein said compound has one or more peaks in its XRPD selected from those at about 10.1, about 12.5, about 15.2, about 19.7, about 20.9, about 23.0, and about 25.3 degrees 2-theta. In some such embodiments, the present disclosure provides compound 1, wherein said compound has at least two peaks in its XRPD selected from those at about 10.1, about 12.5, about 15.2, about 19.7, about 20.9, about 23.0, and about 25.3 degrees 2-theta. In some such embodiments, the present disclosure provides compound 1, wherein said compound is of Form C. In some embodiments, the present disclosure provides compound 1, wherein said compound has an XRPD substantially similar to that depicted in FIG. 1A.

In some embodiments, the present disclosure provides compound 1, wherein said compound has one or more peaks in its XRPD selected from those at about 8.9, about 9.9, about 13.3, about 15.3, about 17.2, about 17.7, about 19.8, about 26.1 degrees 2-theta. In some such embodiments, the present disclosure provides compound 1, wherein said compound has at least two peaks in its XRPD selected from those at about 8.9, about 9.9, about 13.3, about 15.3, about 17.2, about 17.7, about 19.8, about 26.1 degrees 2-theta. In some such embodiments, the present disclosure provides compound 1, wherein said compound is of Form D. In some embodiments, the present disclosure provides compound 1, wherein said compound has an XRPD substantially similar to that depicted in FIG. 2A.

In some embodiments, the present disclosure provides compound 1, wherein said compound has one or more peaks in its XRPD selected from those at about 13.1, about 14.3, about 16.4, about 17.2, about 19.2, and about 24.5 degrees 2-theta. In some such embodiments, the present disclosure provides compound 1, wherein said compound has at least two peaks in its XRPD selected from those at about 13.1, about 14.3, about 16.4, about 17.2, about 19.2, and about 24.5 degrees 2-theta. In some such embodiments, the present disclosure provides compound 1, wherein said compound is of Form E. In some embodiments, the present disclosure provides compound 1, wherein said compound has an XRPD substantially similar to that depicted in FIG. 3A.

In some embodiments, the present disclosure provides compound 1, wherein said compound has one or more peaks in its XRPD selected from those at about 12.9, about 13.2, about 14.1, about 17.9, about 24.6, about 25.4, and about 25.7 degrees 2-theta. In some such embodiments, the present disclosure provides compound 1, wherein said compound has at least two peaks in its XRPD selected from those at about 12.9, about 13.2, about 14.1, about 17.9, about 24.6, about 25.4, and about 25.7 degrees 2-theta. In some such embodiments, the present disclosure provides compound 1, wherein said compound is of Form G. In some embodiments, the present disclosure provides compound 1, wherein said compound has an XRPD substantially similar to that depicted in FIG. 4A.

In some embodiments, the present disclosure provides compound 1, wherein said compound has one or more peaks in its XRPD selected from those at about 8.9, about 9.9, about 13.3, about 15.3, about 17.2, about 17.7, about 19.8, about 26.1 degrees 2-theta. In some such embodiments, the present disclosure provides compound 1, wherein said compound has at least two peaks in its XRPD selected from those at about 8.9, about 9.9, about 13.3, about 15.3, about 17.2, about 17.7, about 19.8, about 26.1 degrees 2-theta. In some such embodiments, the present disclosure provides compound 1, wherein said compound is of Form H. In some embodiments, the present disclosure provides compound 1, wherein said compound has an XRPD substantially similar to that depicted in FIG. 5A.

In some embodiments, the present disclosure provides a composition comprising compound 1 and a pharmaceutically acceptable carrier or excipient.

In some embodiments, the present disclosure provides a method of selectively inhibiting c-kit kinase in a patient comprising administering to said patient compound 1 or a composition thereof. In some embodiments, the method depletes mast cells, thereby treating mast-cell associated diseases.

In some embodiments, the present disclosure provides a method of treating a c-kit kinase mediated disease or disorder in a patient, comprising administering to said patient compound 1 or a composition thereof. In some embodiments, the present disclosure provides a method of treating a mast-cell associated disease or disorder in a patient, comprising administering to said patient compound 1 or a composition thereof.

In some embodiments of the methods above, compound 1 is in Form C, Form D, Form E, Form G or Form H. In some embodiments, compound 1 is in Form C. In some embodiments, compound 1 is in Form D. In some embodiments, compound 1 is in Form E. In some embodiments, compound 1 is in Form G. In some embodiments, compound 1 is in Form H.

Salt Forms of Compound 1

In some embodiments, an acid and compound 1 are ionically bonded to form compound 2 described below. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or a mixture thereof. Exemplary such solid forms of compound 2 are described in more detail below.

Compound 2 (Acetic Acid Salts of Compound 1)

According to one embodiment, the present disclosure provides a acetate salt of compound 1, represented by compound 2:

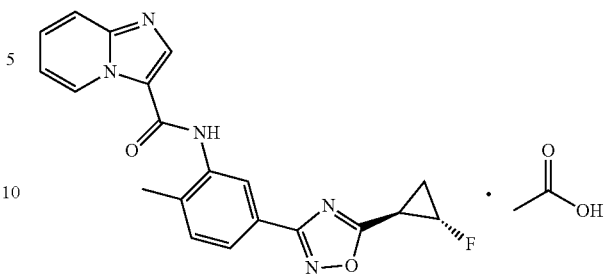

It will be appreciated by one of ordinary skill in the art that the acetic acid and compound 1 are ionically bonded to form compound 2. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or a mixture thereof. Exemplary solid forms are described in more detail below.

In some embodiments, the present disclosure provides a form of compound 2 substantially free of impurities. As used herein, the term "substantially free of impurities" means that the compound contains no significant amount of extraneous matter. Such extraneous matter may include different forms of compound 2, residual solvents, or any other impurities that may result from the preparation of, and/or isolation of, compound 2. In certain embodiments, at least about 95% by weight of a form of compound 2 is present. In still other embodiments of the disclosure, at least about 99% by weight of a form of compound 2 is present.

According to one embodiment, a form of compound 2 is present in an amount of at least about 97, 97.5, 98.0, 98.5, 99, 99.5, 99.8 weight percent where the percentages are based on the total weight of the composition. According to another embodiment, a form of compound 2 contains no more than about 3.0 area percent HPLC of total organic impurities and, in certain embodiments, no more than about 1.5 area percent HPLC total organic impurities relative to the total area of the HPLC chromatogram. In other embodiments, a form of compound 2 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for a form of compound 2 is also meant to include all tautomeric forms of compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this disclosure.

It has been found that compound 2 can exist in a variety of solid forms. Exemplary such forms include polymorphs such as those described herein.

In certain embodiments, compound 2 is a crystalline solid. In other embodiments, compound 2 is a crystalline solid substantially free of amorphous compound 2. As used herein, the term "substantially free of amorphous compound 2" means that the compound contains no significant amount of amorphous compound 2. In certain embodiments, at least about 95% by weight of crystalline compound 2 is present. In still other embodiments of the disclosure, at least about 99% by weight of crystalline compound 2 is present.

It has been found that compound 2 can exist in at least one distinct polymorphic form. In certain embodiments, the present disclosure provides a polymorphic form of compound 2 referred to herein as Form F.

In some embodiments, compound 2 is amorphous. In some embodiments, compound 2 is amorphous, and is substantially free of crystalline compound 2.

Form F of Compound 2

In some embodiments, Form F of compound 2 has at least 1, 2, 3, 4 or 5 spectral peak(s) selected from the peaks listed in Table 6 below.

TABLE 6

XRPD Peak Positions for Form F of Compound 2

| Position (°2θ) | Intensity % |
|---|---|
| 5.1 | 23.9 |
| 7.8 | 36.8 |
| 14.4 | 22.7 |
| 15.7 | 25.0 |
| 17.0 | 17.5 |
| 18.4 | 17.6 |
| 18.9 | 20.4 |
| 19.1 | 29.0 |
| 19.7 | 8.6 |
| 20.3 | 31.7 |
| 20.5 | 10.9 |
| 20.9 | 15.2 |
| 22.0 | 25.9 |
| 22.3 | 15.4 |
| 23.8 | 49.6 |
| 24.6 | 18.2 |
| 25.3 | 29.9 |
| 27.0 | 100.0 |
| 27.6 | 9.9 |
| 29.0 | 7.8 |

In this and all subsequent tables, the position (°2θ) is within ±0.2.

In some embodiments, Form F of compound 2 is characterized in that it has one or more peaks in its X-ray powder diffraction pattern selected from those at about 7.8, about 19.1, about 20.3, about 23.8, about 25.3, and about 27.0 degrees 2-theta. In some embodiments, Form F of compound 2 is characterized in that it has two or more peaks in its X-ray powder diffraction pattern selected from those at about 7.8, about 19.1, about 20.3, about 23.8, about 25.3, and about 27.0 degrees 2-theta. In some embodiments, Form F of compound 2 is characterized in that it has three or more peaks in its X-ray powder diffraction pattern selected from those at about 7.8, about 19.1, about 20.3, about 23.8, about 25.3, and about 27.0 degrees 2-theta. In some embodiments, Form F of compound 2 is characterized in that it has four or more peaks in its X-ray powder diffraction pattern selected from those at about 7.8, about 19.1, about 20.3, about 23.8, about 25.3, and about 27.0 degrees 2-theta. In some embodiments, Form F of compound 2 is characterized in that it has five or more peaks in its X-ray powder diffraction pattern selected from those at about 7.8, about 19.1, about 20.3, about 23.8, about 25.3, and about 27.0 degrees 2-theta. In some embodiments, Form F of compound 2 is characterized in that it has six peaks in its X-ray powder diffraction pattern selected from those at about 7.8, about 19.1, about 20.3, about 23.8, about 25.3, and about 27.0 degrees 2-theta.

In some embodiments, Form F of compound 2 is characterized in that it has each of the spectral peaks in its X-ray powder diffraction pattern listed in Table 6 having a relative intensity greater than 10%, 20%, 30% or 40%. In certain embodiments, the X-ray powder diffraction pattern is substantially similar to the XRPD provided in FIG. 6A.

Methods for preparing Form F of compound 2 are described infra.

In some embodiments, the disclosure provides compound 2:

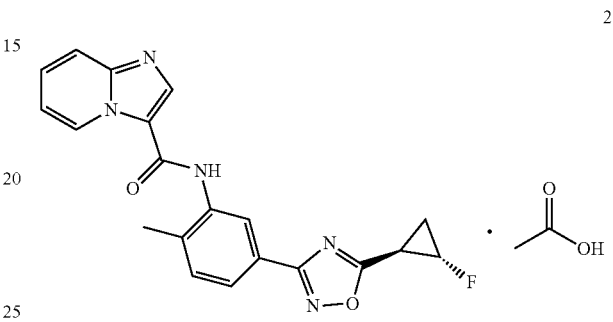

wherein said compound is crystalline. In some embodiments, the present disclosure provides compound 2, wherein said compound is substantially free of amorphous compound 2.

In some embodiments, the present disclosure provides compound 2, wherein said compound is substantially free of impurities.

In some embodiments, the present disclosure provides compound 2, wherein said compound has one or more peaks in its XRPD selected from those at about 7.8, about 19.1, about 20.3, about 23.8, about 25.3, and about 27.0 degrees 2-theta. In some such embodiments, the present disclosure provides compound 2, wherein said compound has at least two peaks in its XRPD selected from those at about 7.8, about 19.1, about 20.3, about 23.8, about 25.3, and about 27.0 degrees 2-theta. In some such embodiments, the present disclosure provides compound 2, wherein said compound is of Form F.

Figure 6A:
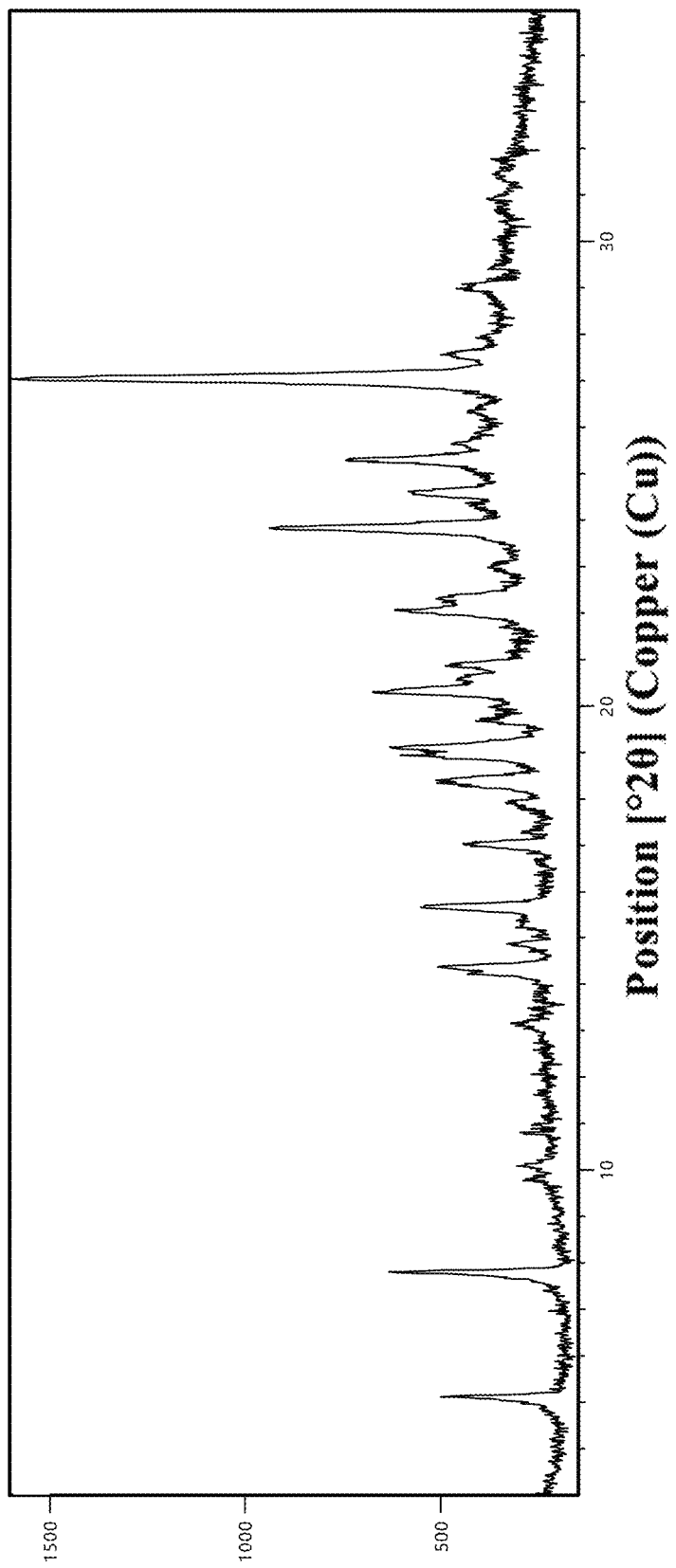
FIG. 6A depicts an XRPD pattern of Form F of compound 2.

In some embodiments, the present disclosure provides compound 2, wherein said compound has an XRPD substantially similar to that depicted in FIG. 6A.

In some embodiments, the present disclosure provides a composition comprising compound 2 and a pharmaceutically acceptable carrier or excipient.

In some embodiments, the present disclosure provides a method of selectively inhibiting c-kit kinase in a patient comprising administering to said patient compound 2 or a composition thereof. In some embodiments, the method depletes mast cells, thereby treating mast-cell associated diseases.

In some embodiments, the present disclosure provides a method of treating a c-kit kinase mediated disease or disorder in a patient, comprising administering to said patient compound 2 or a composition thereof. In some embodiments, the present disclosure provides a method of treating a mast-cell associated disease or disorder in a patient, comprising administering to said patient compound 2 or a composition thereof.

General Methods of Providing Compound 1 and Salts Thereof

Compound 1 can be prepared according example F110 of WO 2013/033070 A1, which is incorporated by reference herein, as summarized in the general Scheme provided below:

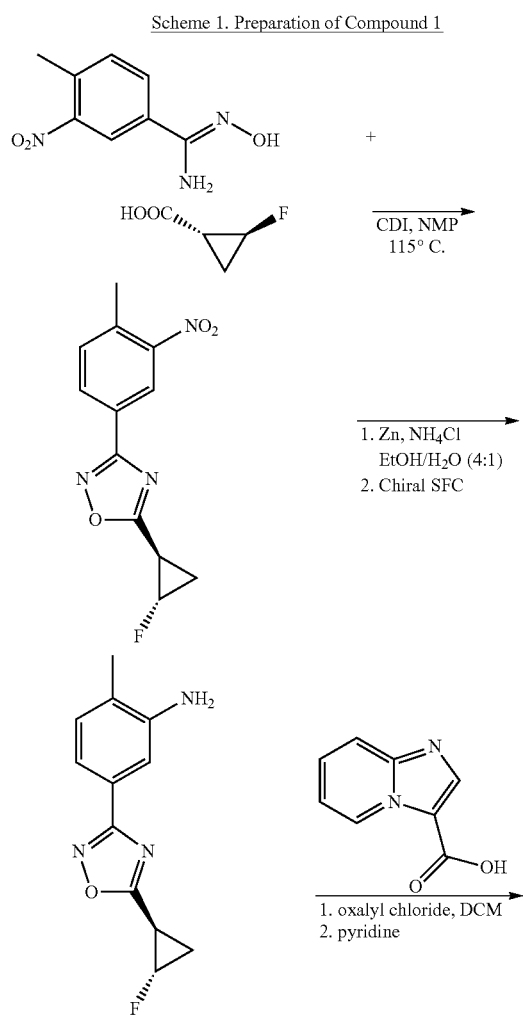

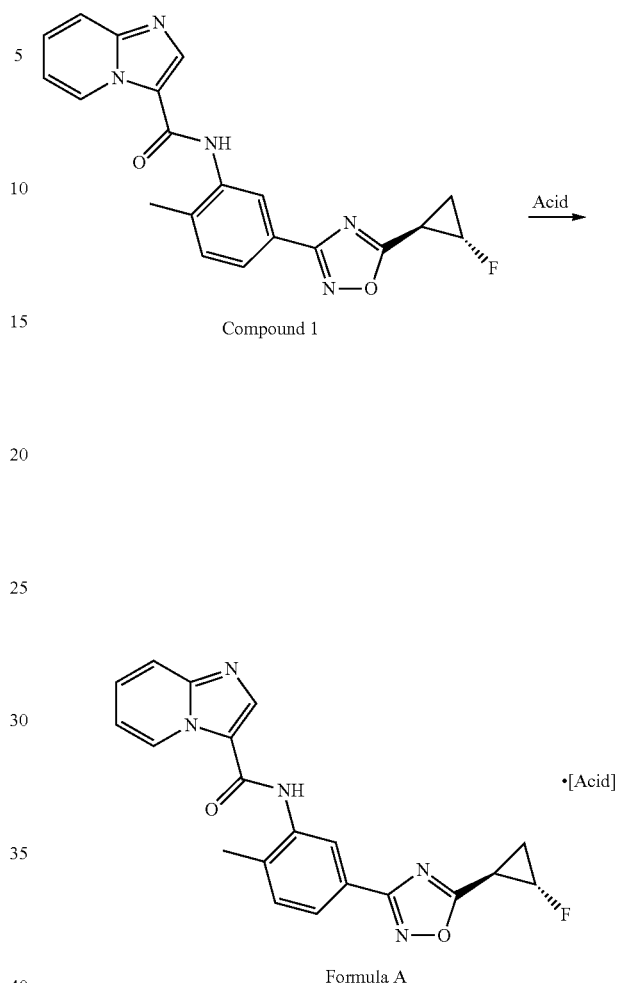

Salt compounds of general formula A, which formula encompasses, inter alia, salt compound 2, and/or particular forms thereof, are prepared from compound 1, according to the methods disclosed in the general Scheme below.

For instance, compound 2, and forms thereof, are prepared from compound 1 by combining compound 1 with an appropriate acid to form a salt of that acid. Thus, another aspect of the present disclosure provides a method for preparing compound 2, and forms thereof.

As described generally above, in some embodiments, the present disclosure provides a method for preparing a salt compound of the general formula A:

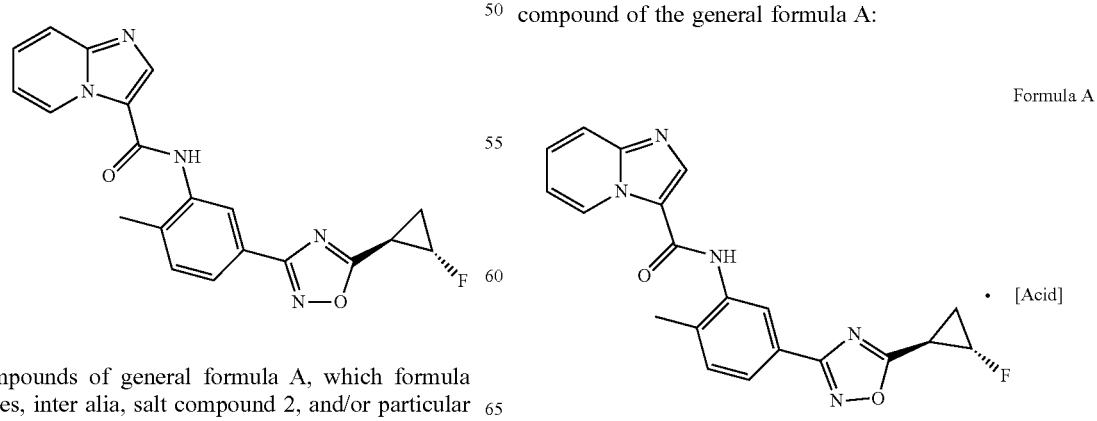

comprising steps of:
combining compound 1:

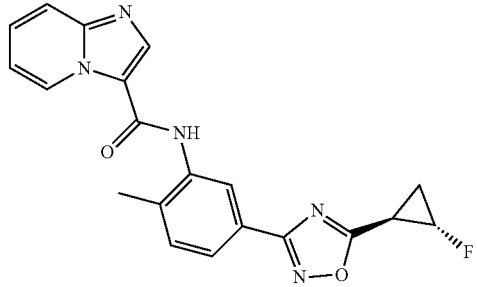

Compound 1 with a suitable acid and optionally a suitable solvent under conditions suitable for forming a salt of formula A.

In some embodiments, a suitable acid is acetic acid. In some embodiments, the present disclosure provides a method of making an acetate salt of compound 1. In certain embodiments, the acetate salt of compound 1 is compound 2. In certain embodiments, the acetate salt of compound 1 is Form F of compound 2.

Uses of Compounds and Pharmaceutically Acceptable Compositions

As described generally above, compound 1, and pharmaceutically acceptable solid forms and salts thereof described herein, are inhibitors of c-kit kinase. The c-kit kinase inhibiting compounds of the present disclosure can, in some embodiments, find use in inhibiting activity of a target c-kit kinase in vitro or in vivo. Aspects of the subject methods include contacting a sample comprising an effective amount of a c-kit kinase inhibiting compound (e.g., as described herein) to determine whether the desired activity exists.

In one aspect, the present disclosure provides methods for treating a c-kit kinase mediated disease or disorder in a subject in need thereof. In some embodiments, the method comprises administering to the subject in need thereof a therapeutically effective amount of a compound as disclosed herein, i.e., a compound selected from compounds 1 and 2 and any polymorphic forms thereof. In some embodiments, the disease or disorder is a mast-cell associated disease, a respiratory disease, an inflammatory disorder, an autoimmune disorder, a metabolic disease, a fibrosis disease, or a dermatological disease. In some embodiments, the disease or disorder is asthma, allergic rhinitis, pulmonary arterial hypertension (PAH), primary pulmonary hypertension (PPH), pulmonary fibrosis, hepatic fibrosis, cardiac fibrosis, scleroderma, irritable bowel syndrome (IBS), inflammatory bowel disease (IBD), urticaria, dermatosis, atopic dermatitis, allergic contact dermatitis, rheumatoid arthritis, multiple sclerosis, melanoma, a gastrointestinal stromal tumor, a mast cell tumor, mastocytosis, anaphylactic syndrome, food allergy, type I diabetes or type II diabetes.

In another aspect, the present disclosure provides a compound as disclosed herein, i.e., a compound selected from compounds 1 and 2 and any polymorphic forms thereof, for use in treating a c-kit kinase mediated disease or disorder in a subject in need thereof. In yet another aspect, the present disclosure provides a compound as disclosed herein, i.e., a compound selected from compounds 1 and 2 and any polymorphic forms thereof, for the manufacture of a medicament for treating a c-kit kinase mediated disease or disorder in a subject in need thereof. In some embodiments, the disease or disorder is a mast-cell associated disease, a respiratory disease, an inflammatory disorder, an autoimmune disorder, a metabolic disease, a fibrosis disease, or a dermatological disease. In some embodiments, the disease or disorder is asthma, allergic rhinitis, pulmonary arterial hypertension (PAH), primary pulmonary hypertension (PPH), pulmonary fibrosis, hepatic fibrosis, cardiac fibrosis, scleroderma, irritable bowel syndrome (IBS), inflammatory bowel disease (IBD), urticaria, dermatosis, atopic dermatitis, allergic contact dermatitis, rheumatoid arthritis, multiple sclerosis, melanoma, a gastrointestinal stromal tumor, a mast cell tumor, mastocytosis, anaphylactic syndrome, food allergy, type I diabetes or type II diabetes.

As used herein, the terms "combination," "combined," and related terms refer to the simultaneous or sequential administration of therapeutic agents in accordance with this disclosure. For example, a described compound may be administered with another therapeutic agent simultaneously or sequentially in separate unit dosage forms or together in a single unit dosage form. Accordingly, the present disclosure provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

When the compounds of this disclosure are administered in combination therapies with other agents, they may be administered sequentially or concurrently to the patient. Alternatively, pharmaceutical or prophylactic compositions according to this disclosure comprise a combination of compound 1, or any other compound described herein, and another therapeutic or prophylactic agent. Additional therapeutic agents that are normally administered to treat a particular disease or condition may be referred to as "agents appropriate for the disease, or condition, being treated."

In some embodiments, the subject method includes administering a therapeutically effective amount of one or more additional active agents. By combination therapy is meant that a c-kit inhibiting compound can be used in a combination with another therapeutic agent to treat a single disease or condition. In particular embodiments, a compound of the present disclosure is administered concurrently with the administration of another therapeutic agent, which can be administered as a component of a composition including the compound of the present disclosure or as a component of a different composition.

The subject compounds can be administered in combination with other therapeutic agents in a variety of therapeutic applications. Therapeutic applications of interest for combination therapy include those applications in which activity of a target c-kit kinase is the cause or a compounding factor in disease progression. As such, the subject compounds find use in combination therapies in which the inhibition of a target c-kit kinase in the subject is desired. The compounds utilized in the compositions and methods of this disclosure may also be modified by appending appropriate functionalities to enhance selective biological properties. Such modifications are known in the art and include those, which increase biological penetration into a given biological system (e.g., blood, lymphatic system, or central nervous system), increase oral availability, increase solubility to allow administration by injection, alter metabolism and/or alter rate of excretion.

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those at risk or needing preventive measures).

The term "subject" as used herein refers to any individual or patient to which the subject methods are performed. Generally, the subject is human, although as will be appreciated by those in the art, the subject may be an animal.

The terms "therapeutically effective amount", "effective dose", "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. In some embodiments, such amount should be sufficient to inhibit a c-kit kinase.

In some embodiments, an effective amount of a c-kit inhibiting compound is an amount that ranges from about 50 ng/ml to 50 μg/ml (e.g., from about 50 ng/ml to 40 μg/ml, from about 30 ng/ml to 20 μg/ml, from about 50 ng/ml to 10 μg/ml, from about 50 ng/ml to 1 μg/ml, from about 50 ng/ml to 800 ng/ml, from about 50 ng/ml to 700 ng/ml, from about 50 ng/ml to 600 ng/ml, from about 50 ng/ml to 500 ng/ml, from about 50 ng/ml to 400 ng/ml, from about 60 ng/ml to 400 ng/ml, from about 70 ng/ml to 300 ng/ml, from about 60 ng/ml to 100 ng/ml, from about 65 ng/ml to 85 ng/ml, from about 70 ng/ml to 90 ng/ml, from about 200 ng/ml to 900 ng/ml, from about 200 ng/ml to 800 ng/ml, from about 200 ng/ml to 700 ng/ml, from about 200 ng/ml to 600 ng/ml, from about 200 ng/ml to 500 ng/ml, from about 200 ng/ml to 400 ng/ml, or from about 200 ng/ml to about ng/ml).

In some embodiments, an effective amount of a c-kit inhibiting compound is an amount that ranges from about 10 μg to 100 mg, e.g., from about 10 μg to 50 μg, from about 50 μg to 150 pg, from about 150 μg to 250 μg, from about 250 μg to 500 μg, from about 500 μg to 750 μg, from about 750 μg to 1 ng, from about 1 ng to 10 ng, from about 10 ng to 50 ng, from about 50 ng to 150 ng, from about 150 ng to 250 ng, from about 250 ng to 500 ng, from about 500 ng to 750 ng, from about 750 ng to 1 mg, from about 1 μg to 10 μg, from about 10 μg to 50 μg, from about 50 pg to 150 μg, from about 150 μg to 250 μg, from about 250 μg to 500 μg, from about 500 μg to 750 μg, from about 750 μg to 1 mg, from about 1 mg to 50 mg, from about 1 mg to 100 mg, or from about 50 mg to 100 mg. The amount can be a single dose amount or can be a total daily amount. The total daily amount can range from about 10 μg to 100 mg, or can range from about 100 mg to 500 mg, or can range from about 500 mg to 1000 mg.

Also disclosed herein are pharmaceutical compositions including compounds as disclosed herein e.g., any one of compounds 1 and 2 and polymorphic forms thereof.

The term "pharmaceutically acceptable carrier" refers to a non-toxic carrier that may be administered to a patient, together with a compound of this disclosure, and which does not destroy the pharmacological activity thereof. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In pharmaceutical compositions comprising only the compounds described herein as the active component, methods for administering these compositions may additionally comprise the step of administering to the subject an additional agent or therapy. Such therapies include, but are not limited to, an anemia therapy, a diabetes therapy, a hypertension therapy, a cholesterol therapy, neuropharmacologic drugs, drugs modulating cardiovascular function, drugs modulating inflammation, immune function, production of blood cells, hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, antivirals, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. Other examples of agents or therapies that can be administered with the compounds described herein include a matrix metalloprotease inhibitor, a lipoxygenase inhibitor, a cytokine antagonist, an immunosuppressant, a cytokine, a growth factor, an immunomodulator, a prostaglandin or an anti-vascular hyperproliferation compound.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Pharmaceutically Acceptable Compositions

The compounds and compositions, according to the method of the present disclosure, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the disclosure are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the disclosure are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

All features of each of the aspects of the disclosure apply to all other aspects mutatis mutandis. Each of the references referred to herein, including but not limited to patents, patent applications and journal articles, is incorporated by reference herein as though fully set forth in its entirety, In order that the disclosure described herein may be more fully understood, the following examples are set forth. It should be understood that these examples are for illustrative purposes only and are not to be construed as limiting this disclosure in any manner.

EXAMPLES

As depicted in the Examples below, in certain exemplary embodiments, compounds are prepared according to the following general procedures. It will be appreciated that, although the general methods depict the synthesis of certain compounds of the present disclosure, the following general methods, and other methods known to one of ordinary skill in the art, can be applied to all compounds and subclasses and species of each of these compounds, as described herein.

Solvent Abbreviations

| Abbreviation | Solvent |
| --- | --- |
| MeOH | Methanol |
| EtOH | Ethanol |
| IPA | Isopropyl alcohol |
| MEK | Methyl ethyl ketone |
| MIBK | 4-Methyl-2-pentanone |

-continued

| Abbreviation | Solvent |
| --- | --- |
| EtOAc | Ethyl acetate |
| IPAc | Isopropyl acetate |
| DMSO | Dimethylsulfoxide |
| MTBE | Methyl tert-butyl ether |
| THF | Tetrahydrofuran |
| 2-MeTHF | 2-Methyltetrahydrofuran |
| CPME | Cyclopentyl methyl ether |
| ACN | Acetonitrile |
| DCM | Dichloromethane |
| DMAc | N,N-Dimethylacetamide |

Analysis Methods
X-ray Powder Diffraction (XRPD) Method A
XRPD patterns were identified with an X-ray diffractometer (PANalytical X'Pert3). The XRPD parameters used are listed in Table A1:

| Parameters | X' Pert3 |
| --- | --- |
| X-Ray wavelength | Cu, Kα, Kα1, (Å): 1.540598; Kα2 (Å): 1.544426 intensity ratio Kα2/Kα1: 0.50 |
| X-Ray tube setting | 45 kV, 40 mA |
| Divergence slit | ⅛° |
| Scan mode | Continuous |
| Scan range (2θ/°) | 3°~40° |
| Step size (2θ/°) | 0.0263° |
| Scan step time (s) | 46.67 |
| Test time | About 5 mins |

X-Ray Powder Diffraction (XRPD) Method B
XRPD analysis was carried out on a PANalytical X'pert pro with PIXcel detector (128 channels), scanning the samples between 3 and 35° 2θ. The material was gently ground to release any agglomerates and loaded onto a multi-well plate with Mylar polymer film to support the sample. The multi-well plate was then placed into the diffractometer and analyzed using Cu K radiation ($\alpha_1$ λ=1.54060 Å; $\alpha_2$=1.54443 Å; β=1.39225 Å; $\alpha_1$:$\alpha_2$ ratio=0.5) running in transmission mode (step size 0.0130° 2θ, step time 18.87 s) using 40 kV/40 mA generator settings. Data were visualized and images generated using the HighScore Plus 4.7 desktop application (PANalytical, 2017).
Thermogravimetric Analysis (TGA) and Differential Scanning Calorimeter (DSC)

Approximately, 5-10 mg of material was added into a pre-tared open aluminum pan and loaded into a TA Instruments Discovery SDT 650 Auto—Simultaneous DSC and held at room temperature. The sample was then heated at a rate of 10° C./min from 30° C. to 350° C. during which time the change in sample weight was recorded along with the heat flow response (DSC). Nitrogen was used as the sample purge gas, at a flow rate of 200 cm³/min.
Dynamic Vapor Sorption (DVS)

Approximately, 10 mg of sample was placed into a mesh vapor sorption balance pan and loaded into a DVS-1/DVS Intrinsic/DVS Advantage dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 min, maximum step length 500 min) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined. XRPD analysis was then carried out on any solid retained.

Proton Nuclear Magnetic Resonance ($^1$H-NMR)

$^1$H Solution NMR was collected on a Bruker 400M NMR Spectrometer or a Bruker AVIIIHD spectrometer equipped with a DCH cryoprobe operating at 500.12 MHz. Samples were prepared in DMSO-d6 at a concentration of about 10 mM.

Water Activity Meter

Water activity measurements were performed on a validated AQUALab TDL Water Activity Monitor Series 4. Two measurements were taken per sample and an average was taken of the two values.

Preparation of Biorelevant Media

Simulated Gastric Fluid (SGF)

About 200 mg of sodium chloride and about 100 mg Triton X-100 was weighted into a 100-mL volumetric flask. About 100 mL of purified water was added to the flask and the solution was sonicated until all solids were completely dissolved. 1 M HCl was added to adjust the pH to 1.8 and the solution was mixed well and the pH was checked with a pH meter.

Fasted State Simulated Intestinal Fluid (FaSSIF)

About 170 mg of sodium phosphate monobasic, about 21 mg of sodium hydroxide and about 310 mg of sodium chloride were weighted into a 50-mL volumetric flask. About 50 mL of purified water was added to the flask and the solution was sonicated until all solids were completely dissolved. The pH was adjusted to pH 6.5. About 22 mg of simulated intestinal fluid (SIF) powder was added into a separate 10-mL volumetric flask. The pH 6.5 buffer solution was added to the 10-mL volumetric flask to reach 10 mL total volume and the solution was mixed well.

Fed State Simulated Intestinal Fluid (FeSSIF)

About 0.41 mg of glacial acetic acid, about 202 mg of sodium hydroxide and about 594 mg of sodium chloride were weighted into a 50-mL volumetric flask. About 50 mL of purified water was added to the flask and the solution was sonicated until all solids were completely dissolved. The pH was adjusted to pH 5.0. About 112 mg of simulated intestinal fluid (SIF) powder was added into a separate 10-mL volumetric flask. The pH 5.0 buffer solution was added to the 10-mL volumetric flask to reach 10 mL total volume and the solution was mixed well.

Example 1: Preparation of Free Base Forms α, $H^A$, $H^B$, C, D, E, G, and H of Compound 1

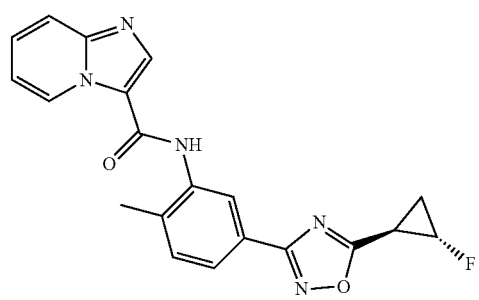

Compound 1

Form A of Compound 1

Form A of compound 1 was prepared as disclosed in PCT/CN2019/086582, which is incorporated by reference herein:

Procedure A: About 2.0 g of amorphous compound 1 (as prepared in Example F110 of WO 2013/033070 A1) was dissolved in 40 mL of IPA at 70° C. and mechanically stirred for 3 hours, resulting in a clear solution. The solution was then cooled to rt and continually stirred overnight. Precipitate formed overnight and was filtered and washed with IPA and dried overnight at 60° C. under vacuum.

Characterization of the resulting material demonstrated crystalline Form A of Compound 1 free base. Based on small TGA weight loss and corresponding DSC signals, Form A was postulated to be an anhydrate.

Table 7, sets forth the X-ray diffraction peaks observed for Form A of compound 1.

TABLE 7

| XRPD Peak Positions for Form A of Compound 1 | |
|---|---|
| Position (°2θ) | Intensity % |
| 5.0 | 11.2 |
| 8.8 | 7.6 |
| 9.8 | 29.3 |
| 10.1 | 17.5 |
| 11.4 | 3.2 |
| 13.2 | 59.7 |
| 15.2 | 100 |
| 17.1 | 17.3 |
| 17.4 | 19.4 |
| 17.6 | 14.4 |
| 18.5 | 9.3 |
| 19.7 | 68.7 |

In this and all subsequent tables, the position (°2θ) is within ±0.2.

Form $H^4$ of Compound 1

Form $H^4$ of compound 1 was prepared as disclosed in PCT/CN2019/086582, which is incorporated by reference herein:

Procedure A: About 200 mg of Form A of compound 1 was dissolved in 3.0 mL of MeOH/H$_2$O (1:1, v/v) and stirred at 1000 rpm at RT for 5 days. The suspension was centrifuged and the solids were dried under vacuum.

Characterization of the resulting material demonstrated crystalline Form $H^4$ of Compound 1 free base. Based on TGA weight loss of 3.8% up to 150° C., corresponding to 0.8 molar water, Form $H^4$ was postulated to be a hydrate or hemi-hydrate.

Table 8, sets forth the X-ray diffraction peaks observed for Form $H^4$ of compound 1.

TABLE 8

| XRPD Peak Positions for Form $H^4$ of Compound 1 | |
|---|---|
| Position (°2θ) | Intensity % |
| 6.4 | 12.4 |
| 8.0 | 4.0 |
| 10.1 | 2.2 |
| 10.7 | 10.4 |
| 12.8 | 100 |
| 13.6 | 37.0 |
| 16.3 | 3.3 |
| 16.8 | 8.0 |
| 18.4 | 7.0 |
| 19.3 | 27.1 |

TABLE 8-continued

XRPD Peak Positions for
Form H$^A$ of Compound 1

| Position (°2θ) | Intensity % |
|---|---|
| 19.9 | 11.3 |
| 21.6 | 2.9 |
| 25.6 | 8.7 |
| 26.9 | 3.5 |
| 32.6 | 3.2 |

In this and all subsequent tables, the position (°2θ) is within ±0.2.

Form H$^B$ of Compound 1

Form H$^B$ of compound 1 was prepared as disclosed in PCT/CN2019/086582, which is incorporated by reference herein:

Procedure A: About 10 mg of Form A of compound 1 was placed in a vial containing water for 2 weeks. The solid was isolated from the suspension and it was observed that Form A had been converted to Form H$^B$.

Characterization of the resulting material demonstrated crystalline Form H$^B$ of Compound 1 free base. Based on TGA weight loss of 5.4% up to 150° C., corresponding to 1.1 molar water, Form H$^B$ was postulated to be a hydrate.

Table 9, sets forth the X-ray diffraction peaks observed for Form H$^B$ of compound 1.

TABLE 9

XRPD Peak Positions for Form H$^B$ of Compound 1

| Position (°2θ) | Intensity % |
|---|---|
| 6.7 | 32.2 |
| 10.1 | 27.0 |
| 10.7 | 24.1 |
| 11.2 | 13.3 |
| 13.6 | 100 |
| 16.5 | 15.4 |
| 18.0 | 73.3 |
| 19.1 | 56.6 |
| 20.2 | 24.0 |
| 23.5 | 35.1 |
| 23.8 | 45.8 |
| 25.0 | 42.4 |
| 26.4 | 54.7 |
| 28.7 | 19.3 |
| 29.7 | 34.5 |

In this and all subsequent tables, the position (°2θ) is within ±0.2.

Form C of Compound 1

Form C of compound 1 was prepared as follows:

Procedure A: Slow Evaporation Screen—About 20 mg of Form A of compound 1 was dissolved in 1.0 mL of MeOH in a 3-mL glass vial. The sample was shaken and the suspension was filtered using a PTFE membrane (pore size of 0.45 m). The filtrate was slowly evaporated at RT with vials sealed by Parafilm®, poked with several pin-holes. The resulting solids were isolated for XRPD analysis.

Procedure B: Room Temperature Slurry Screen—About 20 mg of Form A of compound 1 was suspended in 0.5 mL of water in an HPLC vial. After the suspension was stirred magnetically (~1000 rpm) for about 7 days at RT, the remaining solids were isolated for XRPD analysis.

Procedure C: Form A of compound 1 (201.2 mg) was suspended in 3.0 mL H$_2$O and stirred at 1000 rpm at RT for 5 days. The suspension was filtered and the solids were dried under vacuum.

Characterization of the resulting material demonstrated crystalline Form C of Compound 1 free base.

Table 1, supra, is reproduced below and sets forth the X-ray diffraction peaks observed for Form C of compound 1.

TABLE 1

XRPD Peak Positions for Form C of Compound 1

| Position (°2θ) | Intensity % |
|---|---|
| 3.2 | 4.6 |
| 10.1 | 12.8 |
| 10.9 | 5.0 |
| 11.6 | 10.4 |
| 12.5 | 100.0 |
| 13.4 | 15.8 |
| 14.1 | 7.9 |
| 14.7 | 18.1 |
| 15.2 | 20.0 |
| 16.3 | 5.2 |
| 17.0 | 10.3 |
| 17.5 | 7.9 |
| 17.8 | 2.7 |
| 19.7 | 13.1 |
| 20.1 | 7.3 |
| 20.9 | 14.6 |
| 21.3 | 7.6 |
| 22.0 | 4.7 |
| 22.3 | 8.4 |
| 23.0 | 26.7 |
| 23.7 | 4.4 |
| 24.3 | 2.7 |
| 25.3 | 11.4 |
| 25.8 | 7.3 |
| 27.1 | 7.2 |
| 27.8 | 5.8 |
| 28.1 | 6.5 |
| 28.5 | 4.4 |
| 29.4 | 6.0 |
| 31.0 | 7.6 |
| 31.9 | 5.2 |
| 32.7 | 1.5 |
| 33.6 | 0.8 |
| 34.2 | 1.7 |
| 36.1 | 0.1 |
| 37.2 | 0.1 |

FIG. 1A depicts an XRPD pattern of Form C of compound 1.

Figure 1B:
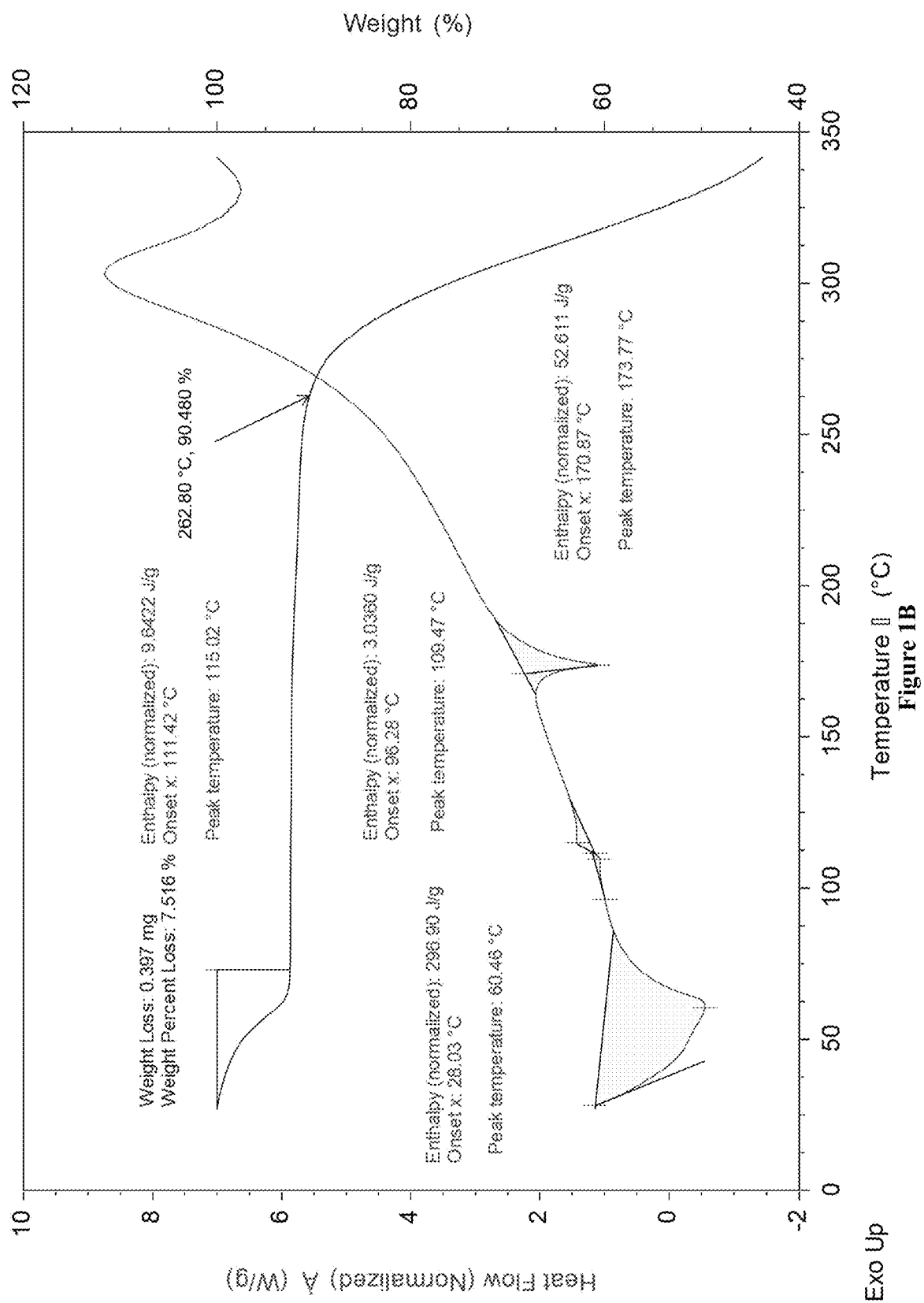
FIG. 1B depicts a DSC thermogram and TGA trace of Form C of compound 1.

FIG. 1B depicts a DSC thermogram and TGA trace of Form C of compound 1. The DSC thermogram of Form C of compound 1 was characterized by endothermic peaks at about 96° C. and about 171° C. and an exothermic peak at about 111° C. Without intending to be limited to any particular theory, it is proposed that the weak events at about 96° C. and about 111° C. can be attributed to melting of Form C and recrystallization into Form A, and the sharp endothermic event at about 171° C. is due to melting of Form A. A weight loss of 7.5% up to 100° C. was observed on the TGA curve, which corresponds to 1.7 molar water loss, suggesting that Form C is a dihydrate.

Figure 1C:
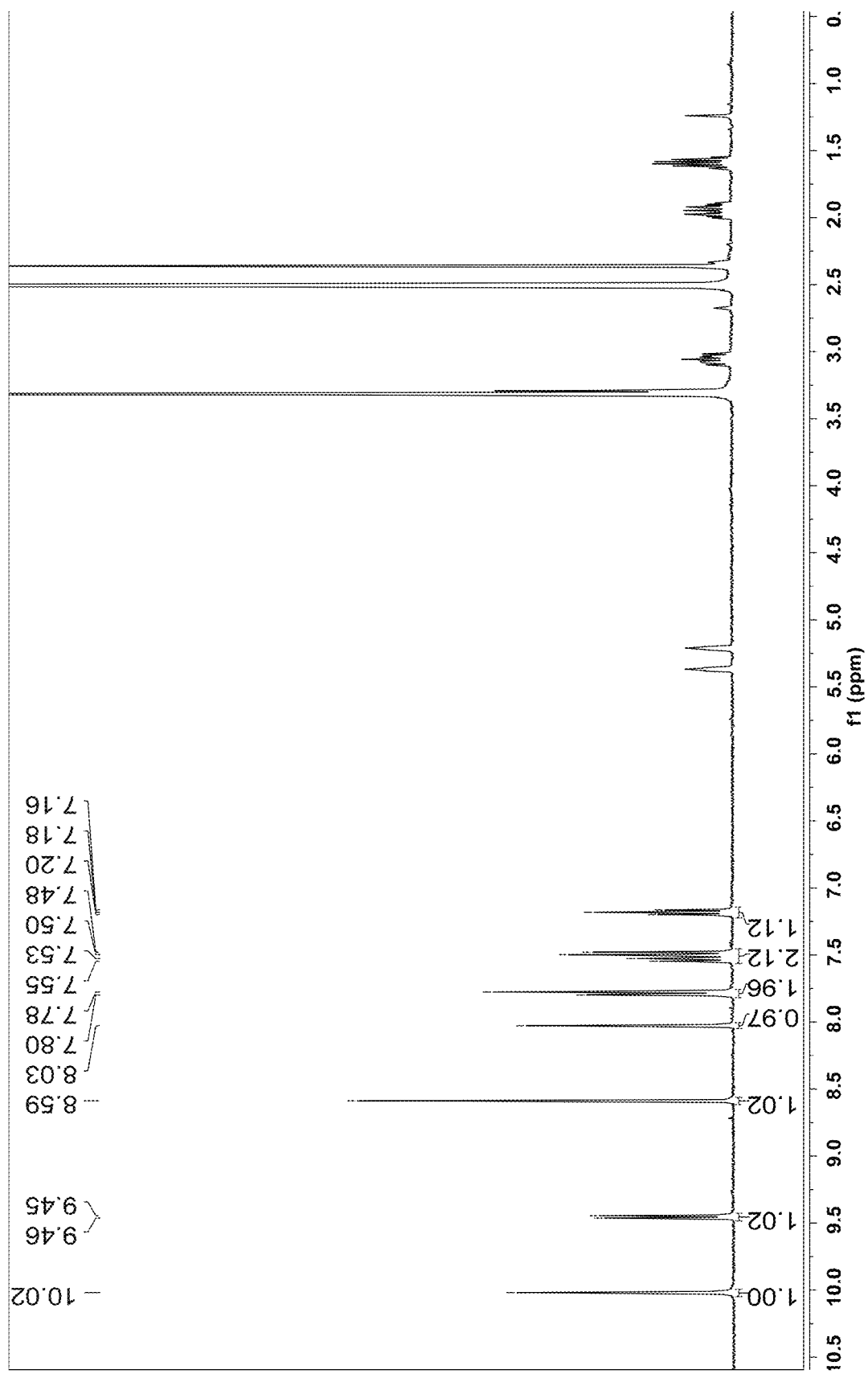
FIG. 1C depicts a $^1$H-NMR spectrum of From C of compound 1.

FIG. 1C depicts a 1H-NMR spectrum of Form C of compound 1.

Figure 1D:
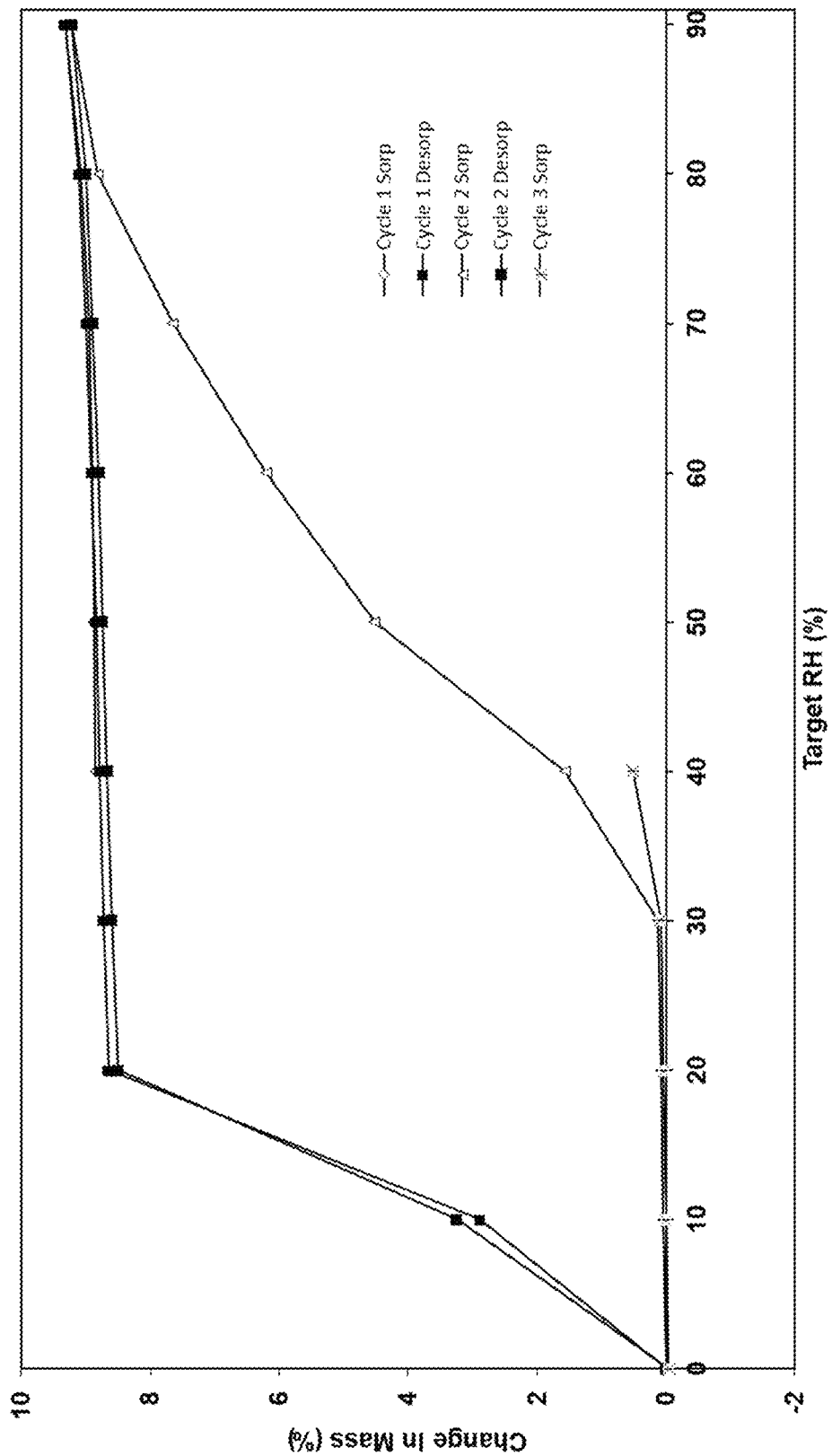
FIGS. 1D and 1E depict DVS plots of Form C of compound 1.
Figure 1E:
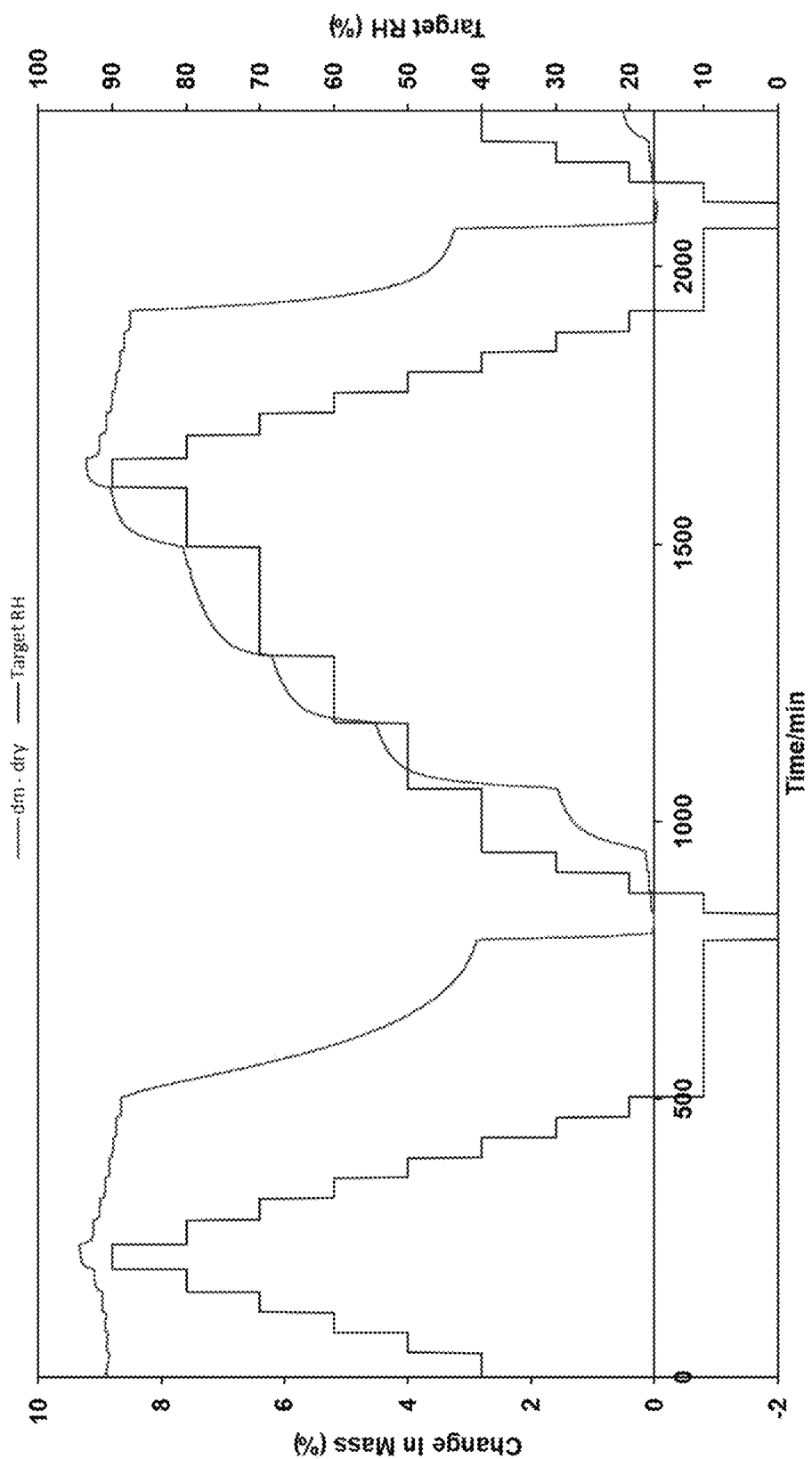

FIGS. 1D and 1E depict DVS plots of Form C of compound 1. Form C was rehydrated up to about 80% RH, experiencing a total mass uptake of 0.6% between 20% and 90% RH, and showed mass loss below 20% RH. Below 20% RH, Form C experienced a mass loss of 8.6%, about equal to 2 equivalents of water.

Figure 1F:
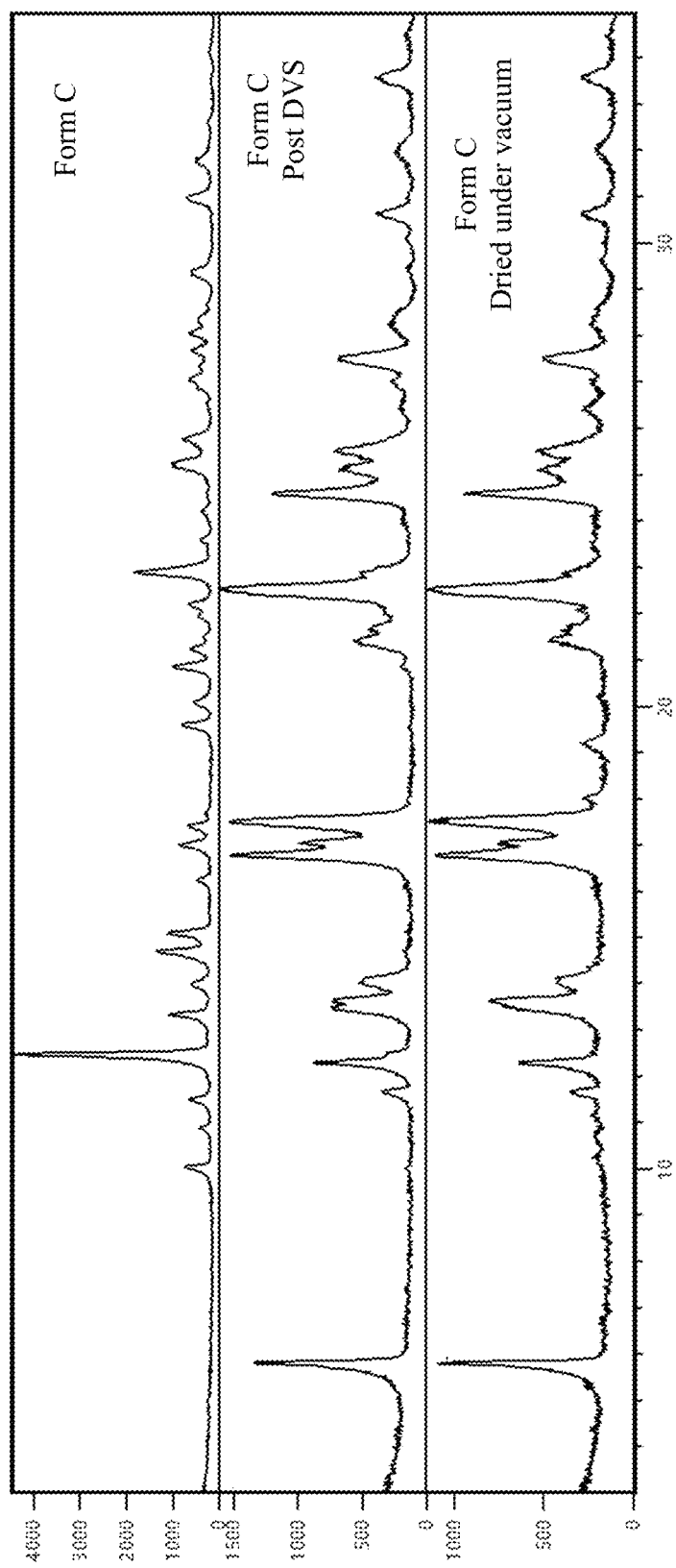
FIG. 1F depicts a set of XRPD patterns of Form C of compound 1, in original form, after DVS experiments and after being dried under vacuum.

FIG. 1F depicts a set of XRPD patterns of Form C of compound 1, comparing the originally isolated form, material after DVS experiments and material after being dried under vacuum. After DVS, Form C converted into Form G of compound 1. Form G was also observed after vacuum drying of Form C.

Form D of Compound 1

Form D of compound 1 was prepared as follows:

Procedure A: 50° C. Slurry Screen—About 20 mg of Form A of compound 1 was suspended in 0.5 mL of IPA in an HPLC vial. The sample was stirred magnetically (~1000 rpm) for about 7 days at 50° C., the remaining solids were isolated for XRPD analysis.

Procedure B: 50° C. Slurry Screen—About 20 mg of Form A of compound 1 was suspended in 0.5 mL of CPME in an HPLC vial. The sample was stirred magnetically (~1000 rpm) for about 7 days at 50° C., the remaining solids were isolated for XRPD analysis.

Procedure C: Anti-solvent addition screen—About 20 mg of Form A of compound 1 was dissolved in DCM to obtain a clear solution and the solution was magnetically stirred (~1000 rpm) followed by addition of MTBE until precipitate appeared. The obtained precipitate was isolated for XRPD analysis.

Procedure D: Anti-solvent addition screen—About 20 mg of Form A of compound 1 was dissolved in pyridine to obtain a clear solution and the solution was magnetically stirred (~1000 rpm) followed by addition of EtOAc until precipitate appeared. The obtained precipitate was isolated for XRPD analysis.

Procedure E: 204.5 mg of Form A of compound 1 was suspended in 3.0 mL IPA and stirred at 1000 rpm at RT for 5 days. The suspension was centrifuged and the solids were dried under vacuum.

Characterization of the resulting material demonstrated crystalline Form D of Compound 1 free base.

Table 2, supra, is reproduced below and sets forth the X-ray diffraction peaks observed for Form D of compound 1.

TABLE 2

XRPD Peak Positions for Form D of Compound 1

| Position (°2θ) | Intensity % |
|---|---|
| 3.1 | 14.1 |
| 5.1 | 8.8 |
| 8.9 | 34.7 |
| 9.9 | 80.7 |
| 10.2 | 9.5 |
| 11.4 | 4.8 |
| 13.3 | 71.7 |
| 15.3 | 46.3 |
| 17.2 | 90.7 |
| 17.7 | 61.8 |
| 18.6 | 28.2 |
| 19.8 | 100.0 |
| 20.4 | 10.6 |
| 21.3 | 2.5 |
| 22.1 | 17.2 |
| 22.9 | 10.8 |
| 24.6 | 3.9 |
| 26.1 | 28.0 |
| 26.9 | 4.2 |
| 27.6 | 5.1 |
| 27.9 | 2.5 |
| 29.9 | 2.4 |
| 31.4 | 2.2 |
| 32.0 | 0.8 |
| 33.0 | 1.5 |
| 34.3 | 2.0 |
| 34.7 | 2.0 |

FIG. 2A depicts an XRPD pattern D Form D of compound 1.

Figure 2B:
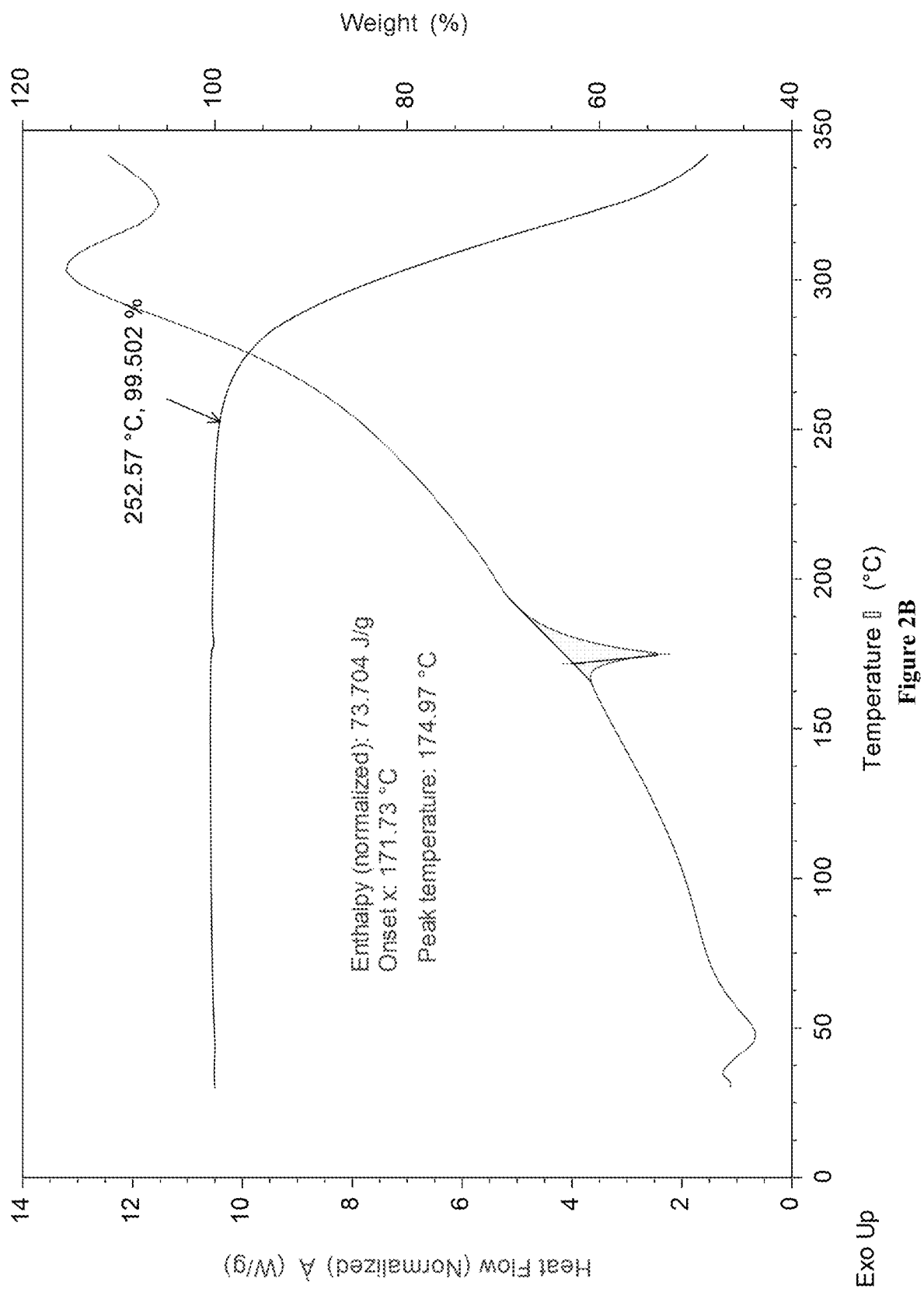
FIG. 2B depicts a DSC thermogram and TGA trace of Form D of compound 1.

FIG. 2B depicts a DSC thermogram and TGA trace of Form D of compound 1. The DSC thermogram of Form D of compound 1 was characterized by an endothermic peak at about 175° C. Minimal weight loss was observed up to about 250° C. on the TGA curve, suggesting that Form D is an anhydrate.

Figure 2C:
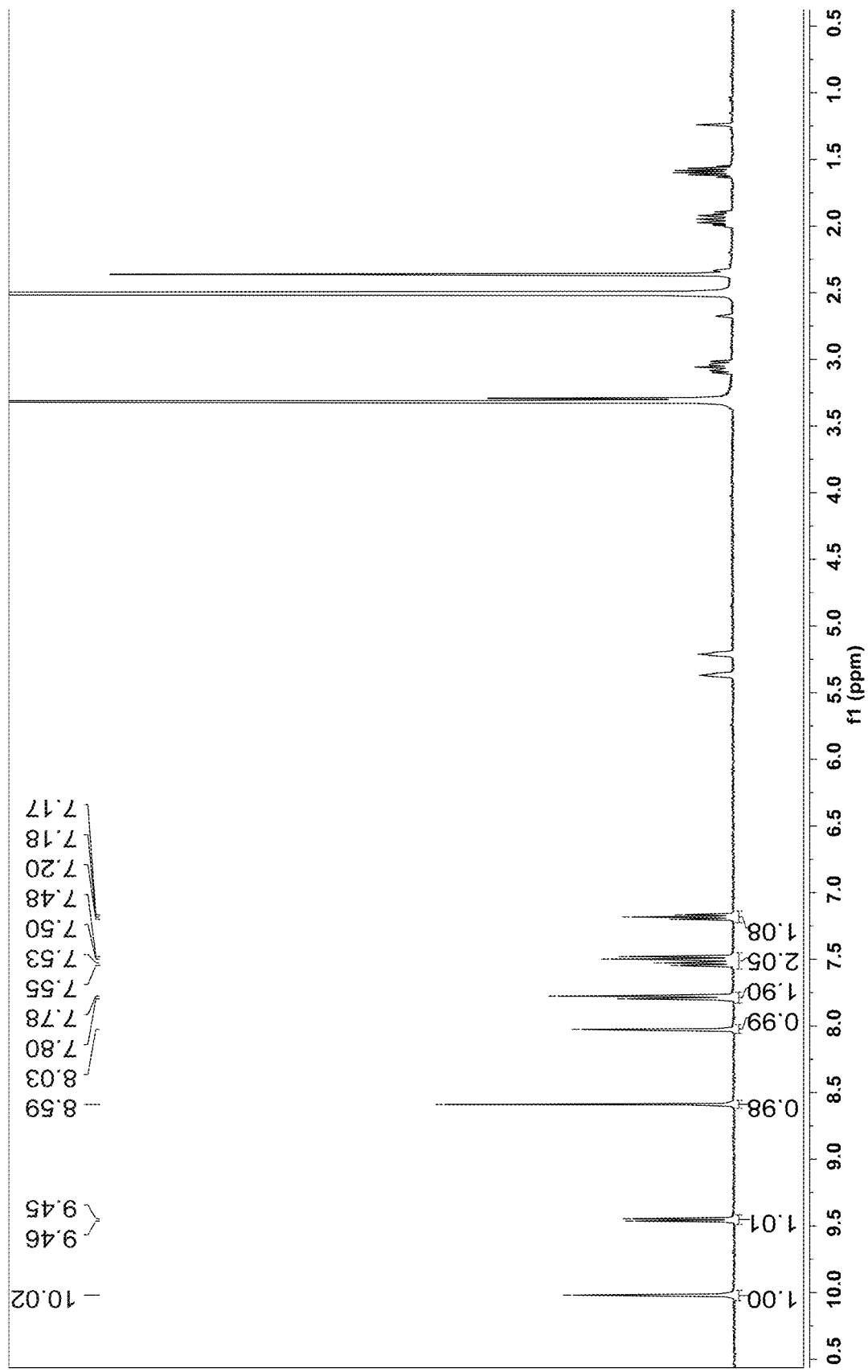
FIG. 2C depicts a $^1$H-NMR spectrum of From D of compound 1.
Figure 2D:
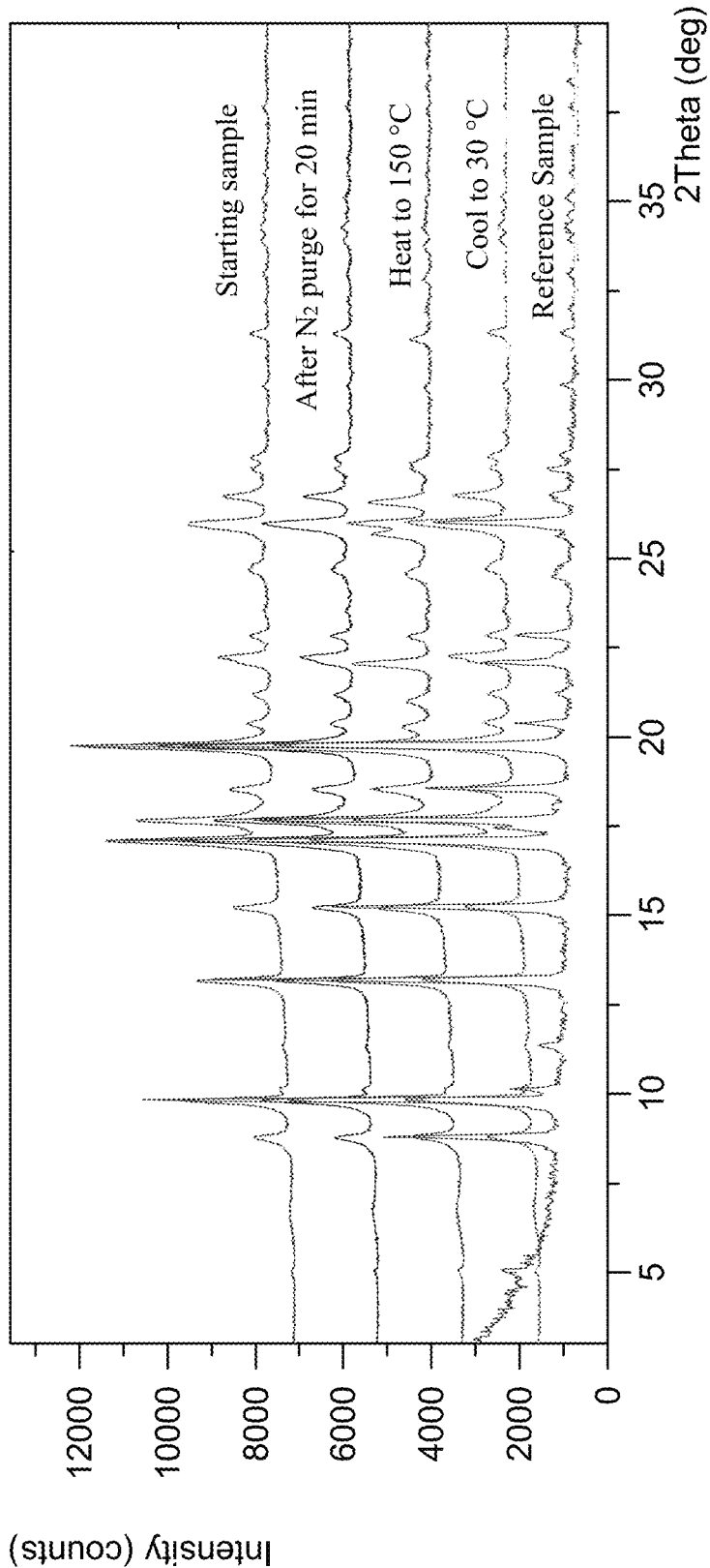
FIG. 2D depicts a variable temperature XRPD of Form D of compound 1.

FIG. 2C depicts a $^1$H-NMR spectrum of Form D of compound 1. The $^1$H-NMR spectrum showed no residual IPA FIG. 2D depicts a variable temperature XRPD of Form D of compound 1. The variable temperature experiment was conducted to further investigate the weight loss observed in the TGA curve. The VT-XRPD showed no form change upon heating to 150° C. or cooling to 30° C. under $N_2$ purge, therefore Form D of compound 1 was postulated to be an anhydrate.

Form E of Compound 1

Form E of compound 1 was prepared as follows:

Procedure A: 20 mg of Form A of compound 1 or amorphous compound 1 was added to a vial containing 1 mL of EtOH/heptane (50:50% v/v) to form a slurry. The vial was agitated for 24 hours at 25° C. After 24 hours, the solids were isolated via centrifugal filtration.

Characterization of the resulting material demonstrated crystalline Form E of Compound 1 free base.

Table 3, supra, is reproduced below and sets forth the X-ray diffraction peaks observed for Form E of compound 1.

TABLE 3

XRPD Peak Positions for Form E of Compound 1

| Position (°2θ) | Intensity % |
|---|---|
| 4.8 | 12.9 |
| 9.5 | 17.6 |
| 10.9 | 25.4 |
| 13.1 | 33.8 |
| 14.3 | 58.3 |
| 14.8 | 14.3 |
| 16.4 | 65.6 |
| 16.6 | 9.5 |
| 17.0 | 20.9 |
| 17.2 | 31.2 |
| 18.8 | 13.9 |
| 19.1 | 17.7 |
| 19.2 | 36.1 |
| 24.5 | 100.0 |
| 25.5 | 9.4 |
| 25.8 | 14.0 |
| 26.3 | 14.4 |
| 26.4 | 10.2 |
| 27.7 | 11.3 |
| 28.4 | 17.5 |

FIG. 3A depicts an XRPD pattern of Form E of compound 1.

Figure 3B:
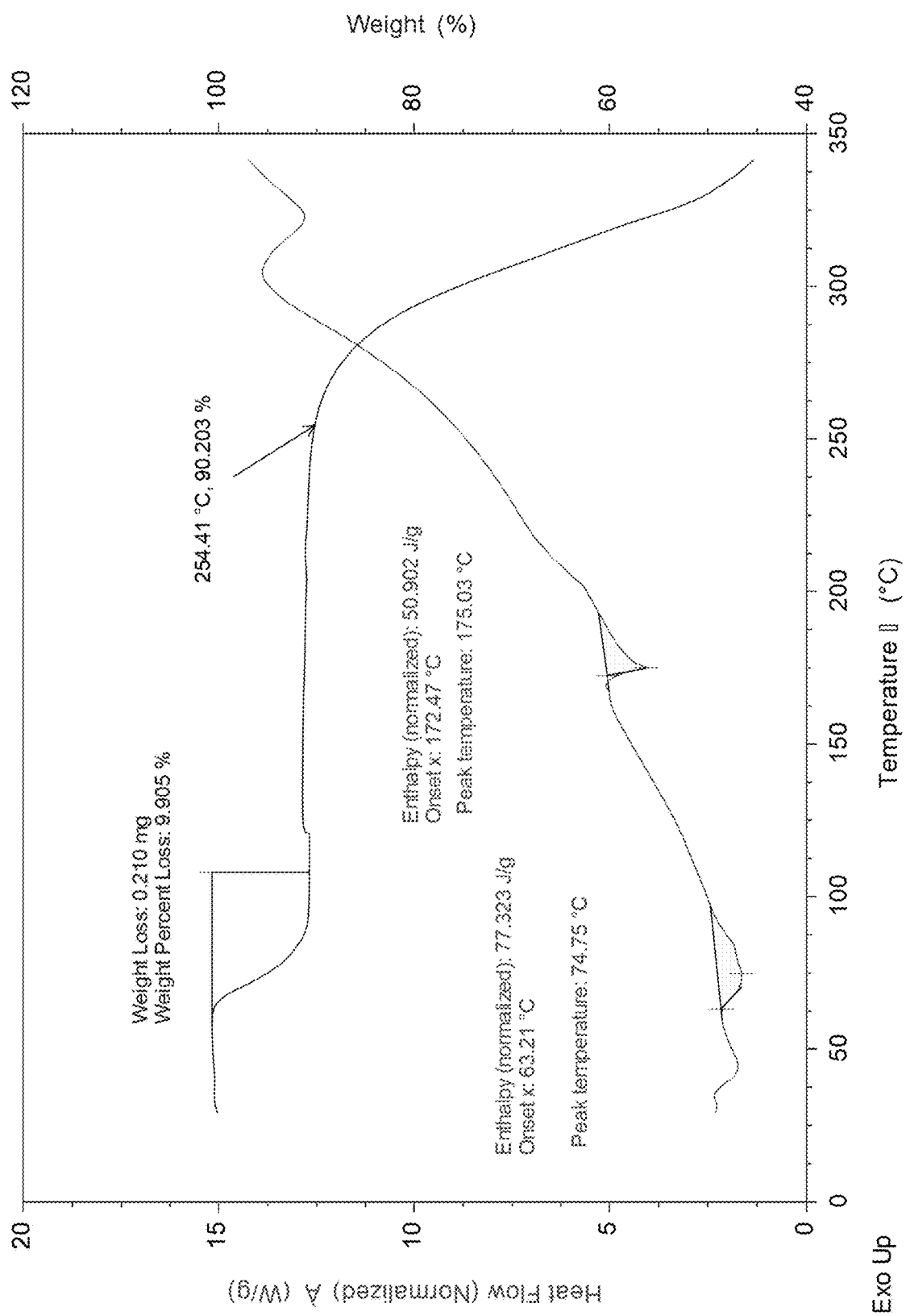
FIG. 3B depicts a DSC thermogram and TGA trace of Form E of compound 1.

FIG. 3B depicts a DSC thermogram and TGA trace of Form E of compound 1. The DSC thermogram of Form E of compound 1 was characterized by endothermic peaks at about 63° C. and about 172° C. A weight loss of 9.9% up to 100° C. was observed on the TGA curve, which equates to about 0.9 equivalents of EtOH. Without intending to be limited to any particular theory, the weight loss and endothermic event at 63° C. can be attributed to desolvation of EtOH.

Figure 3C:
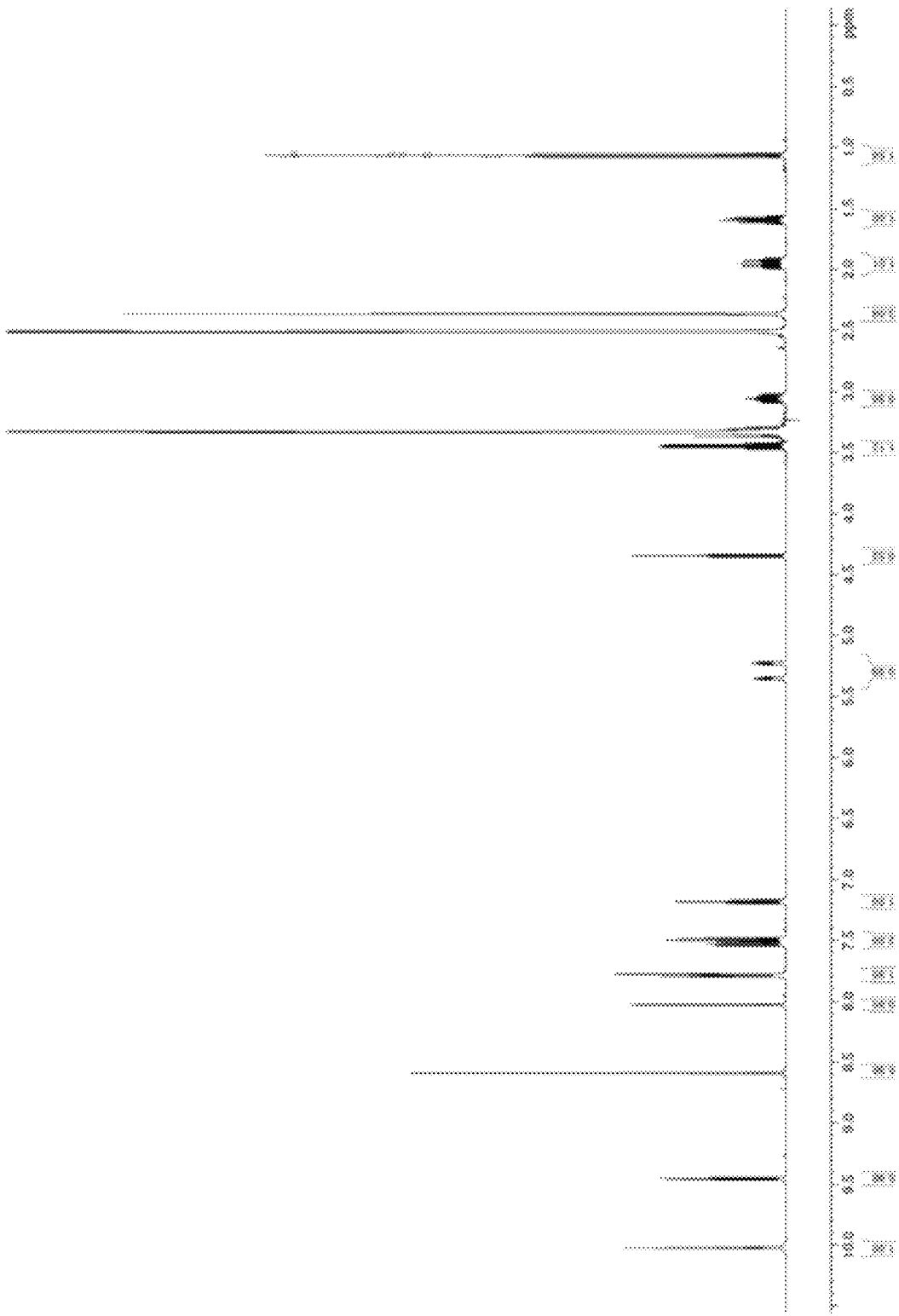
FIG. 3C depicts a $^1$H-NMR spectrum of From E of compound 1.
Figure 3D:
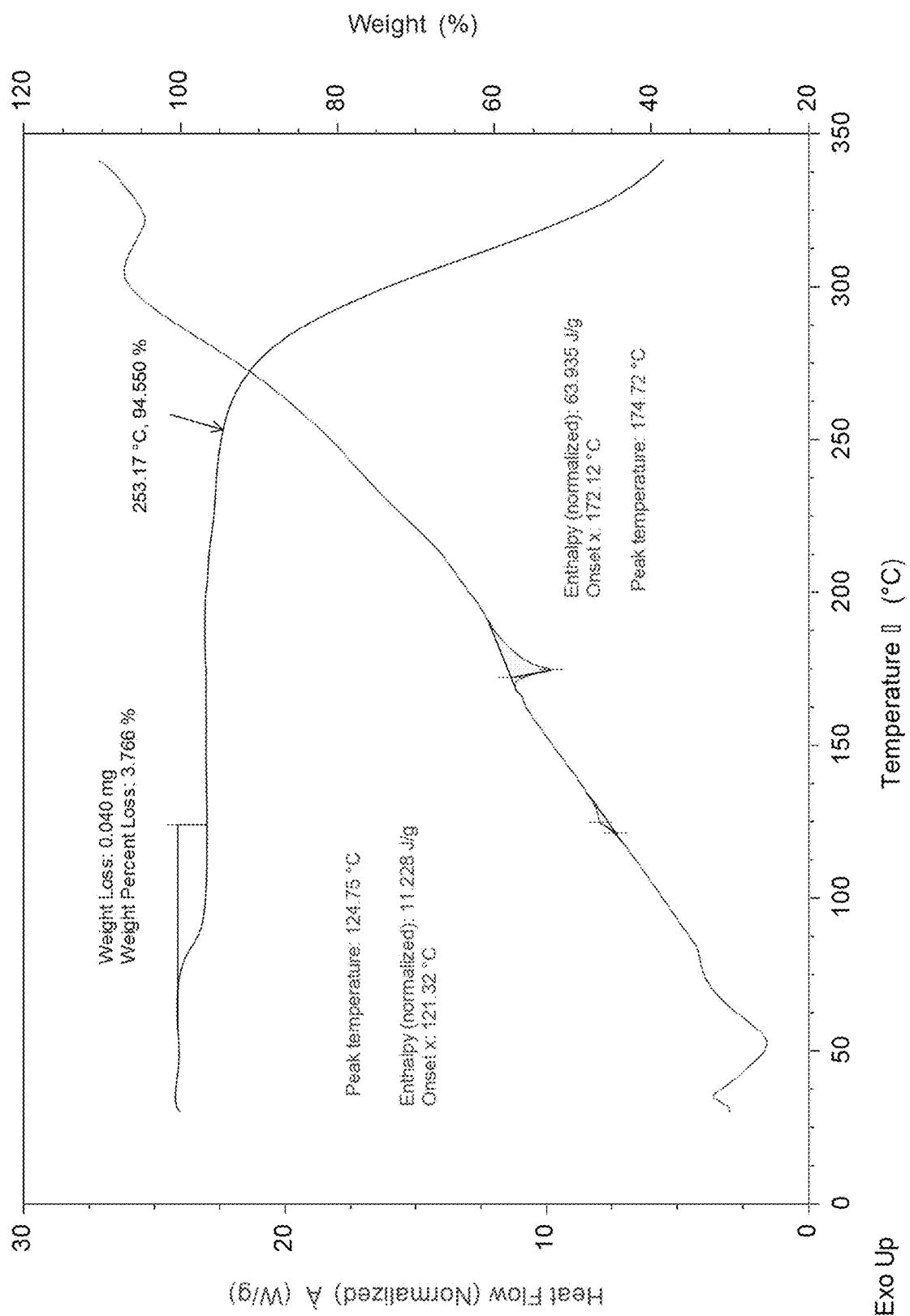
FIG. 3D depicts a DSC thermogram and TGA trace of Form E of compound 1 after drying.

FIG. 3C depicts a $^1$H-NMR spectrum of Form E of compound 1.

Form G of Compound 1

Form G of compound 1 was prepared as follows:

Procedure A: Form C of compound 1 was dried under vacuum at 40° C. for about 2 hours. After drying Form G was recovered.

Characterization of the resulting material demonstrated crystalline Form G of Compound 1 free base.

Table 4, supra, is reproduced below and sets forth the X-ray diffraction peaks observed for Form G of compound 1.

TABLE 4

XRPD Peak Positions for Form G of Compound 1

| Position (°2θ) | Intensity % |
|---|---|
| 5.8 | 85.1 |
| 11.7 | 15.2 |
| 12.3 | 54.2 |
| 13.5 | 42.5 |
| 13.7 | 42.0 |
| 14.0 | 26.4 |
| 14.1 | 25.2 |
| 16.8 | 100.0 |
| 17.0 | 62.5 |
| 17.5 | 97.1 |
| 21.4 | 27.5 |
| 21.7 | 20.1 |
| 22.6 | 93.0 |
| 24.6 | 74.5 |
| 25.1 | 33.9 |
| 25.5 | 40.4 |
| 27.5 | 38.6 |
| 28.2 | 10.3 |
| 30.6 | 18.3 |
| 33.6 | 18.3 |

FIG. 4A depicts an XRPD pattern of Form G of compound 1.

Figure 4B:
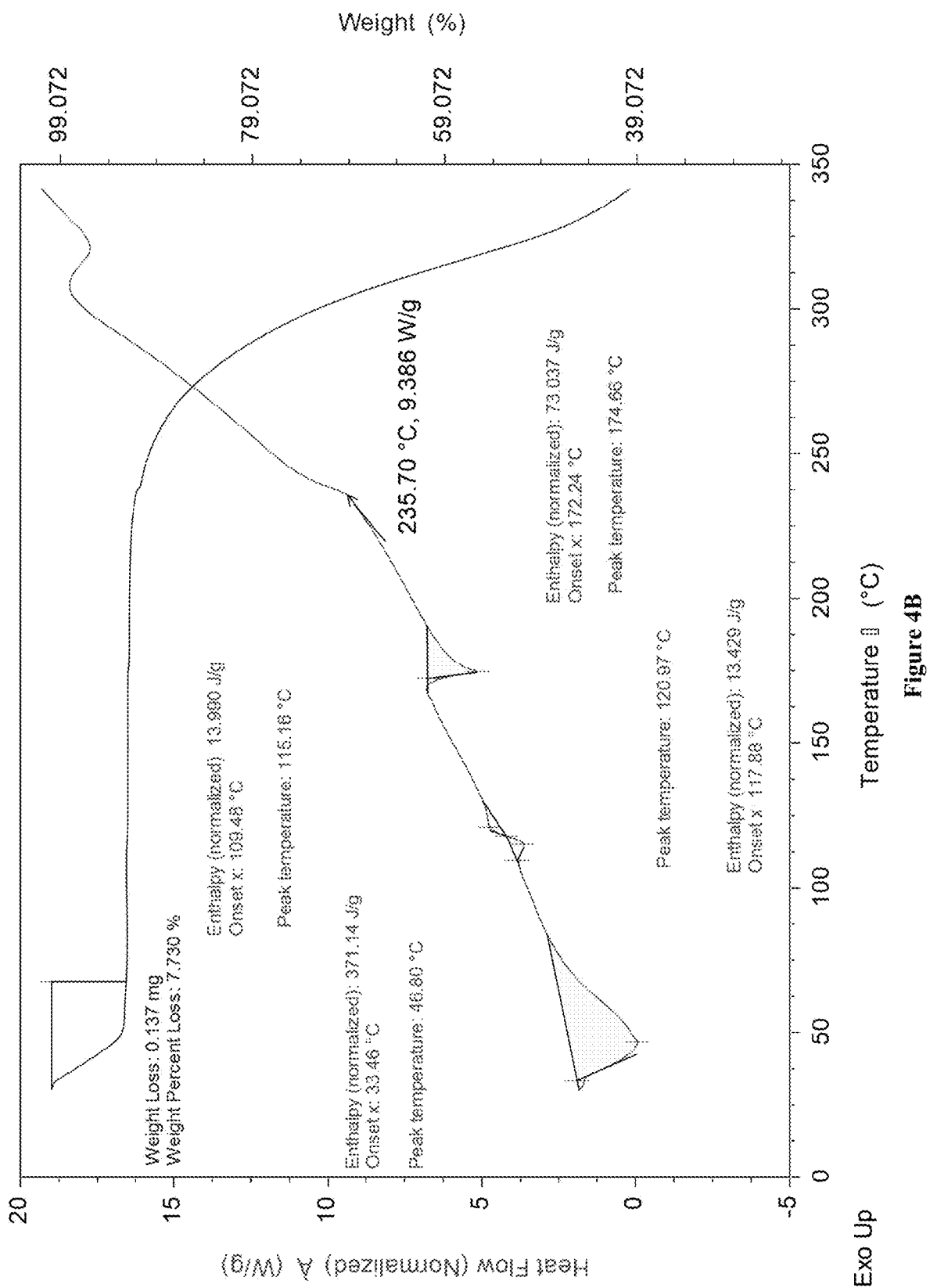
FIG. 4B depicts a DSC thermogram and TGA trace of Form G of compound 1.

FIG. 4B depicts a DSC thermogram and TGA trace collected from a sample of Form G of compound 1. The DSC thermogram of collected was characterized by endothermic peaks at about 109° C. and about 172° C. and an exothermic peak at about 118° C. A weight loss of 7.7% up to 100° C. was observed on the TGA curve. Without intending to be limited to any particular theory, it is proposed that Form G is a metastable anhydrous form which readily rehydrates to Form C under ambient conditions, based on the fact that the DSC thermogram and TGA trace collected from the sample of Form G of compound 1 closely resembles the DSC thermogram and TGA trace collected for Form C.

Form H of Compound 1

Form H of Compound 1 was prepared as follows:

Procedure A: 20 mg of Form A was added to vials containing MeOH/H$_2$O solutions having a water activity (a$_w$) of 0.5145 or 0.6965. The slurries were agitated for 24 h at 25° C. After 24 h, aliquots of the solid were isolated via centrifugal filtration and analyzed by XRPD. The remaining slurry samples were agitated for a further 5 days (6 days in total). The solids were isolated after 6 days and analyzed by XRPD. Form H was observed in the 24 h aliquots of both the 0.5145 and 0.6965 MeOH/H$_2$O solutions, and in the 6 day sample from the 0.6965 MeOH/H$_2$O solution.

Procedure B: 20 mg of amorphous compound 1 was added to a vial containing aMeOH/H$_2$O solution having a water activity (a$_w$) of 0.3242. The slurry were agitated for 72 h at 25° C. After 72 h, the solids were isolated via centrifugal filtration and analyzed by XRPD. Form H was observed in the 24 h aliquots of both the 0.5145 and 0.6965 MeOH/H$_2$O solutions, and in the 6 day sample from the 0.6965 MeOH/H$_2$O solution.

Characterization of the resulting material demonstrated crystalline Form H of Compound 1 free base.

Table 5, supra, is reproduced below and sets forth the X-ray diffraction peaks observed for Form H of compound 1.

TABLE 5

XRPD Peak Positions for Form H of Compound 1

| Position (°2θ) | Intensity % |
|---|---|
| 7.1 | 10.1 |
| 9.9 | 23.1 |
| 12.9 | 56.9 |
| 13.2 | 53.3 |
| 14.1 | 58.9 |
| 14.6 | 18.5 |
| 15.7 | 21.8 |
| 16.1 | 13.0 |
| 17.2 | 23.3 |
| 17.9 | 59.7 |
| 18.8 | 36.2 |
| 19.4 | 11.7 |
| 20.0 | 23.7 |
| 21.3 | 22.7 |
| 24.6 | 100.0 |
| 25.4 | 73.1 |
| 25.7 | 74.5 |
| 26.8 | 13.5 |
| 27.2 | 19.3 |
| 29.7 | 10.4 |

FIG. 5A depicts an XRPD pattern of Form H of compound 1.

Figure 5B:
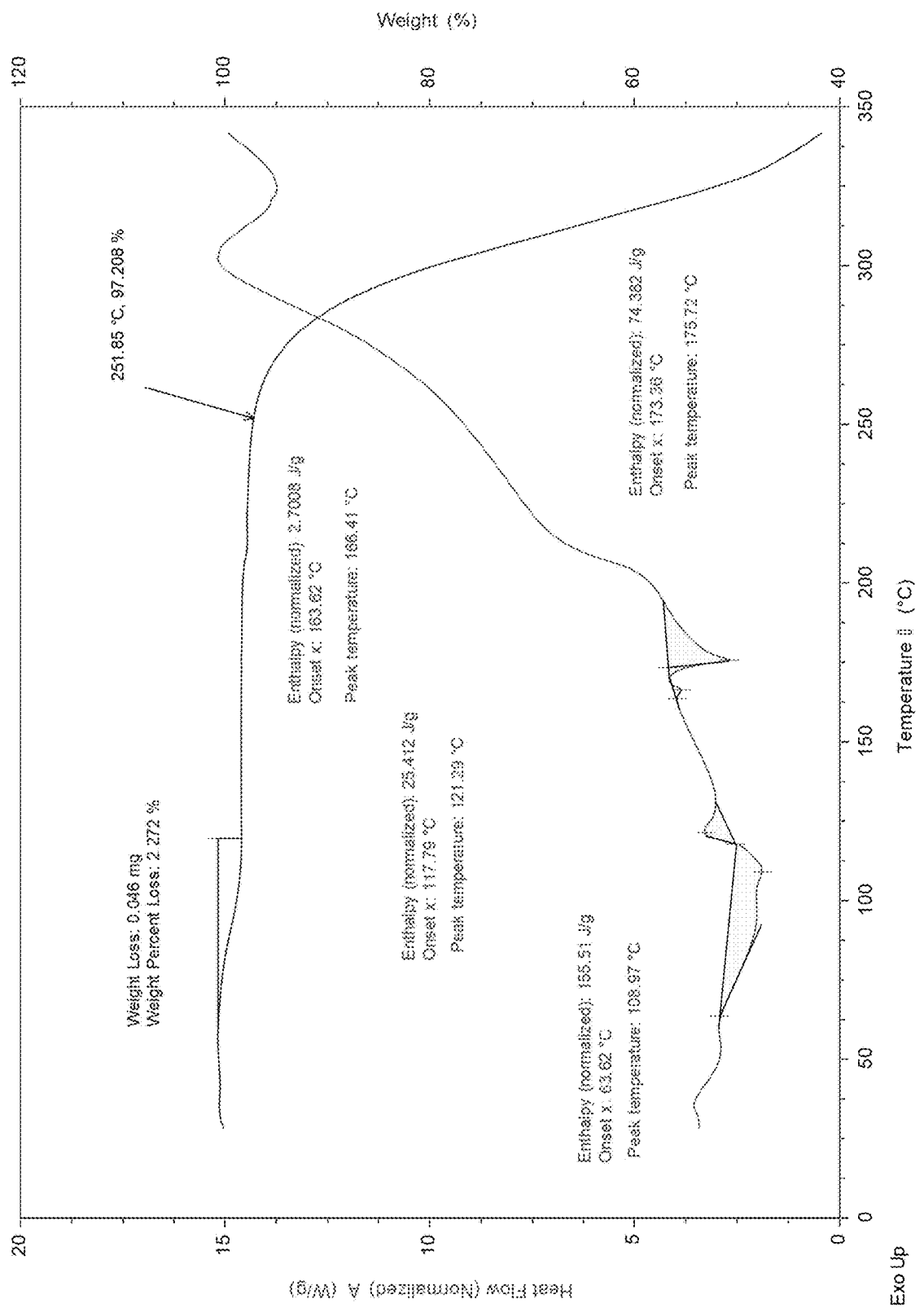
FIG. 5B depicts a DSC thermogram and TGA trace of Form H of compound 1.

FIG. 5B depicts a DSC thermogram and TGA trace of Form H of compound 1. The DSC thermogram of Form H of compound 1 was characterized by an endothermic peaks at about 63° C. and about 173° C. and an exothermic peak at about 118° C. A weight loss of 2.3% up to 100° C. was observed on the TGA curve. Without intending to be limited by any particular theory, the 2.3% weight loss can be attributed to loss of approximately 0.3 equivalents of methanol or 0.5 equivalents of water.

FIG. 5C depicts a $^1$H-NMR spectrum of Form H of compound 1. The NMR data suggests that approximately 0.1 equiv. of MeOH was present in the isolated material.

Example 2: Preparation of Acetic Acid Salt Form F of Compound 2

Form F of Compound 2

Form F of compound 2 was prepared as follows:

Procedure A: 20 mg of Form A of compound 1 or 20 mg of amorphous compound 1 were added to 1 mL of pH 4.5 acetate buffer solution to form a slurry. The slurry was agitated for 24 h at 25° C. After 24 h, acetate salt Form F of compound 2 was isolated from the slurry via centrifugal filtration and analyzed by XRPD.

Characterization of the resulting material demonstrated crystalline Form F of Compound 2.

Table 6, supra, is reproduced below and sets forth the X-ray diffraction peaks observed for Form F of compound 2.

TABLE 6

XRPD Peak Positions for Form F of Compound 2

| Position (°2θ) | Intensity % |
|---|---|
| 5.1 | 23.9 |
| 7.8 | 36.8 |

TABLE 6-continued

XRPD Peak Positions for Form F of Compound 2

| Position (°2θ) | Intensity % |
|---|---|
| 14.4 | 22.7 |
| 15.7 | 25.0 |
| 17.0 | 17.5 |
| 18.4 | 17.6 |
| 18.9 | 20.4 |
| 19.1 | 29.0 |
| 19.7 | 8.6 |
| 20.3 | 31.7 |
| 20.5 | 10.9 |
| 20.9 | 15.2 |
| 22.0 | 25.9 |
| 22.3 | 15.4 |
| 23.8 | 49.6 |
| 24.6 | 18.2 |
| 25.3 | 29.9 |
| 27.0 | 100.0 |
| 27.6 | 9.9 |
| 29.0 | 7.8 |

FIG. 6A depicts an XRPD pattern of Form F of compound 2.

Example 3: Inter-Conversion Study of Crystal Forms

Competitive Slurry Experiments Among Anhydrates

Competitive slurry experiments were performed in IPA/IPAc at RT/50° C. between anhydrates Form A of compound 1 and Form D of compound 1. Form A of compound 1 was added into each solvent to form a slurry at RT or 50° C. and was stirred for 2 h. The slurries were then filtered to obtain saturated solution. Around 10 mg each of Form A of compound 1 and Form D of compound 1 were added into each solution to form a mixed slurry at RT or 50° C. As summarized in Table 9, Form $H^A$ of compound 1 or Form D of compound 1 were obtained from the slurries, indicating Form $H^A$ and Form D were thermodynamically more stable than Form A at RT and 50° C. The formation of Form $H^A$ of compound 1 is postulated to be caused by residual water in the solvents or due to ambient humidity (~35% humidity during slurry experiments).

TABLE 10

Competitive slurry experiment between anhydrate forms

| Starting material | Solvent | Temperature | Time (day) | Result |
|---|---|---|---|---|
| Form D + Form A | IPA | RT | 4 | Form D + Form $H^A$ |
| | IPAc | RT | 4 | Form $H^A$ |
| | IPA | 50° C. | 1 | Form D |
| | IPAc | 50° C. | 1 | Form D |

Alternative Competitive Slurry Experiments Among Anhydrates

Competitive slurry experiments were performed in ethanol/heptane (50:50 v/v) or 2-MeTHF at 25° C. Form A of compound 1 (20 mg) was added into each solvent to form a slurry and was agitated for 6 h at 25° C. The slurries were then filtered via centrifugal filtration to remove the solids, in order to obtain saturated solutions. To the saturated solution was added 5 mg each of Form A, Form D and Form E of compound 1. The resulting slurries were agitated for 6 h at 25° C. After 24 h, both slurries yielded Form $H^A$.

Competitive Slurry Experiments Among Anhydrates and Hydrates

Competitive slurry experiments were performed in IPA with varied water content at RT among anhydrate Form D, and hydrate Forms $H^A$, $H^B$ and C. Form A of compound 1 was added into each solution to form a slurry at RT and was stirred for 2 h. The slurries were then filtered to obtain saturated solutions. About 5 mg of each of Forms $H^A$, $H^B$, C and D were added into each solution to form a slurry at RT. As summarized in Table 10, Form $H^A$ was obtained from slurries with $a_w$ 0.2~0.8 after 4 days. A mixture of Form D and Form $H^A$ was obtained from the 100% IPA slurry after 20 days, and a mixture of Form C and Form $H^A$ was obtained from the 100% $H_2O$ slurry after 20 days.

TABLE 11

Competitive slurry experiment between anhydrate and hydrate forms

| Starting material | Solvent (v/v) | Time (day) | Result |
|---|---|---|---|
| Form $H^A$, | IPA | 20 | Form $H^A$ + Form D |
| Form $H^B$, | IPA/$H_2O$ (98:2, $a_w$~0.2) | 4 | Form $H^A$ |
| Form C | IPA/$H_2O$ (96:4, $a_w$~0.4) | 4 | Form $H^A$ |
| and | IPA/$H_2O$ (92:8, $a_w$~0.6) | 4 | Form $H^A$ |
| Form D | IPA/$H_2O$ (85:15, $a_w$~0.8) | 4 | Form $H^A$ |
| | $H_2O$ | 20 | Form $H^A$ + Form C |

Slurry Experiments in SGF

Competitive slurry experiments were performed for Forms A, $H^A$, $H^B$, C and D in SGF. About 10 mg of each form was added into separate HPLC vials followed by addition of 1.0 mL SGF in order to form slurries. The slurries were heated to 37° C. and stirred at 500 rpm. After 2 h or 24 h, the samples were centrifuged and the solids were collected for XRPD testing. The results are summarized in Table 11. No form change was observed after 2 h and 24 h in SGF for Form $H^A$, Form $H^B$ and Form C. Form A transformed to Form C in SGF after 2 h and 24 h. Form D transformed to Form C in SGF after 2 h, and a mixture of Form C and an HCl salt form was observed after 24 h.

TABLE 12

Competitive slurry experiments in SGF

| Starting material | XRPD at 2 h | XRPD at 24 h |
|---|---|---|
| Form $H^A$ | Form $H^A$ | Form $H^A$ |
| Form $H^B$ | Form $H^B$ | Form $H^B$ |
| Form C | Form C | Form C |
| Form D | Form C | Form C + HCl salt form |
| Form A | Form C | Form C |

Example 4: Hydration Mapping and Buffer Media Experiments

To establish the hydration map of compound 1, solutions with varying water activity ($a_w$) were prepared and the $a_w$ was measured using a water activity meter. Table 13 below details the solvent systems investigated and their corresponding measured water activities.

TABLE 13

Solvent systems investigated in hydration mapping study

| Solvent System | Calculated Water Activity ($a_w$) | Organic Solvent (μL) | Water (μL) | Average Water Activity ($a_w$) |
|---|---|---|---|---|
| 2-MeTHF | — | — | — | 0.0378 |
| Water/2-MeTHF (1:99% v/v) | — | 3960 | 40 | 0.5286 |
| EtOH/heptane (50:50% v/v) | — | 2000 | 2000 | 0.0300 |
| Ethanol/water | 0.153 | 3968 | 82 | 0.1580 |
|  | 0.384 | 3868 | 232 | 0.377 |
|  | 0.507 | 3716 | 384 | 0.4986 |
|  | 0.719 | 2736 | 1264 | 0.7600 |
|  | 0.910 | 1060 | 2940 | 0.9005 |
| Acetone/water | 0.136 | 8120 | 100 | 0.1363 |
|  | 0.281 | 3976 | 44 | 0.2621 |
|  | 0.572 | 3920 | 200 | 0.5455 |
|  | 0.713 | 3620 | 660 | 0.7082 |
|  | 0.919 | 1252 | 8348 | 0.9439 |
| Methanol/water | 0.114 | 3908 | 172 | 0.0963 |
|  | 0.335 | 3600 | 550 | 0.3242 |
|  | 0.514 | 3088 | 1112 | 0.5145 |
|  | 0.700 | 2192 | 2208 | 0.6965 |
|  | 0.905 | 800 | 6200 | 0.9294 |
| MeCN/water | 0.105 | 3988 | 12 | 0.1060 |
|  | 0.385 | 3928 | 72 | 0.3664 |
|  | 0.567 | 3852 | 148 | 0.5573 |
|  | 0.724 | 3684 | 316 | 0.7300 |
|  | 0.912 | 1360 | 5140 | 0.8946 |

Hydration Mapping Starting with Form A

23×20 mg of Form A of compound 1 was weighed into vials. 1 mL of solvent (see tables above) was added to each vial to form a slurry. After manual shaking for a few seconds, where solutions were observed, an additional ~10 to 20 mg of solid was added to produce a slurry. Additional solid was added to the 2-MeTHF, water/2-MeTHF (1:99% v/v), acetone/water ($a_w$ of 0.92) and methanol/water ($a_w$ of 0.11) samples. All slurries were then agitated for 24 h at 25° C. After 24 h, aliquots of solid were isolated via centrifugal filtration and analysed by XRPD. The remaining slurries were agitated for a further 5 days (total of 6 days). The solids were isolated and analysed by XRPD. All identified forms were analysed by XRPD, TG/DSC and $^1$H NMR (where sufficient material was available). The results of these hydration mapping experiments are shown below in Table 14.

TABLE 14

XRPD patterns observed in hydration mapping study starting with Form A

| Solvent System | $a_w$ | 24 h | 6 Days |
|---|---|---|---|
| 2-MeTHF | 0.0378 | Form A | Form A |
| EtOH/Heptane | 0.0300 | Form A | Form A |
| EtOH/Water | 0.1580 | Form $H^4$ | Form $H^4$ |
|  | 0.3377 | Form $H^4$ | Form $H^4$ |
|  | 0.4986 | Form $H^4$ | Form $H^4$ |
|  | 0.7600 | Form $H^4$ | Form $H^4$ |
|  | 0.9005 | Form A | Form $H^4$ and possibly Forms C and E |
| Acetone/Water | 0.1363 | Form $H^4$ | Form $H^4$ |
|  | 0.2621 | Form $H^4$ | Form $H^4$ |
|  | 0.5455 | Form $H^4$ | Form $H^4$ |
|  | 0.7082 | Form $H^4$ with addt'l. peaks | Form $H^4$ |
|  | 0.9349 | Form A and Form $H^4$ | Form C and Form $H^4$ and addt'l. peaks |

TABLE 14-continued

XRPD patterns observed in hydration mapping study starting with Form A

| Solvent System | $a_w$ | 24 h | 6 Days |
|---|---|---|---|
| Water/2-MeTHF | 0.5286 | Form $H^4$ | Form $H^4$ |
| MeOH/Water | 0.0963 | Form $H^4$ | Form $H^4$ |
|  | 0.3242 | Form $H^4$ | Form $H^4$ |
|  | 0.5145 | Form H | Form $H^4$ |
|  | 0.6965 | Form H | Form H |
|  | 0.9294 | Form A | Form C |
| MeCN/Water | 0.1060 | Form $H^4$ | Form $H^4$ |
|  | 0.3664 | Form $H^4$ | Form $H^4$ |
|  | 0.5573 | Form $H^4$ | Form $H^4$ |
|  | 0.7300 | Form $H^4$ with addt'l. peaks | Form $H^4$ |
|  | 0.8946 | Form $H^4$ with addt'l. peaks | Form $H^4$ and possibly Form C |

Hydration Mapping Starting with Amorphous Compound 1

To prepare amorphous material, 480 mg of Form A of compound 1 was weighed into a vial before being dissolved in 24 mL 1,4-dioxane. The resulting solution was then split evenly between 24 vials before being placed in the chamber of a freeze dryer at −50° C. to completely freeze the samples. The samples were then freeze dried overnight (approx. 18 h) and fluffy off-white solids were recovered. A small subsample of solid from one vial was analyzed by XRPD to confirm that amorphization had occurred. Using the other 23 vials of amorphous material, 1 mL of the solutions prepared above was added to each vial to prepare slurries. As before, where solutions were observed a brief manual agitation, an additional ~10 to 20 mg of amorphous material was added to prepare a slurry. Additional solid was added to the 2-MeTHF, acetone/water ($a_w$ of 0.14 and 0.28), methanol/water ($a_w$ of 0.11) and acetonitrile/water ($a_w$ of 0.11) samples. All slurries were then agitated for 72 h at 25° C. After 72 h, aliquots of solid were isolated via centrifugal filtration and analyzed by XRPD. The results of these hydration mapping experiments are shown below in Table 15.

TABLE 15

XRPD patterns observed in hydration mapping study starting with Amorphous Compound 1

| Solvent System | $a_w$ | 72 h |
|---|---|---|
| 2-MeTHF | 0.0378 | Forms A, $H^4$ and D |
| EtOH/Heptane | 0.0300 | Form E |
| EtOH/Water | 0.1580 | Form $H^4$ |
|  | 0.3377 | Form $H^4$ |
|  | 0.4986 | Form $H^4$ |
|  | 0.7600 | Form A and Form $H^4$ and additional peaks |
|  | 0.9005 | Form A and Form $H^4$ and additional peaks |
| Acetone/Water | 0.1363 | Form $H^4$ |
|  | 0.2621 | Form $H^4$ |
|  | 0.5455 | Form $H^4$ |
|  | 0.7082 | Form $H^4$ |
|  | 0.9439 | Form $H^4$ and possibly Form C |
| Water/2-MeTHF | 0.5286 | Form $H^4$ |
| MeOH/Water | 0.0963 | Form $H^4$ |
|  | 0.3242 | Form H |
|  | 0.5145 | Form $H^4$ |
|  | 0.6965 | Form H |
|  | 0.9294 | Form C |
| MeCN/Water | 0.1060 | Form $H^4$ |
|  | 0.3664 | Form $H^4$ |
|  | 0.5573 | Form $H^4$ |
|  | 0.7300 | Form $H^4$ |
|  | 0.8946 | Form $H^4$ |

Ethanol/Hydrocarbon Mixtures

Using the methods described above for the Form A input and amorphous input experiments, 5×20 mg of Form A slurries and 5×20 mg of amorphous input slurries were prepared by adding 1 mL of solvent (see Table 16 below) to each vial and the resulting slurries were agitated for 24 h at 25° C. After 24 h, aliquots of solid were isolated via centrifugal filtration and analysed by XRPD. The results of these hydration mapping experiments are shown below in Table 16.

TABLE 16

XRPD patterns observed in ethanol/hydrocarbon study

| Solvent System (50:50% v/v) | $a_w$ | Form A input | Amorphous input |
|---|---|---|---|
| EtOH/Cyclohexane | 0.025 | Form A | Form E |
| EtOH/Dodecane | 0.024 | Form A | Form $H^A$ |
| EtOH/Hexane | 0.018 | Form A | Form E |
| EtOH/Methylcyclohexane | 0.019 | Form A | Form E |
| EtOH/Octane | 0.019 | Form A | Form E |

Example 5: Form Investigation in Buffered Media

To investigate the polymorphic landscape of compound 1 in buffered systems, 5×20 mg of Form A slurries and 5×20 mg of amorphous slurries (amorphous material prepared using the method described in the above hydration mapping experiments) were prepared by adding 1 mL of buffer to each vial and the resulting slurries were agitated for 24 h at 25° C. The pH was measured post-buffer addition and after 24 h agitation. After 24 h, aliquots of solid were isolated via centrifugal filtration and analysed by XRPD.

TABLE 17

Resulting pH of buffered media

| | pH (Post-Buffer Addition) | | pH (24 h) | |
|---|---|---|---|---|
| Solvent System | Amorphous input | Form A input | Amorphous input | Form A input |
| pH 1.2 (HCl—KCl) | 1.21 | 1.20 | 1.21 | 1.19 |
| pH 4.5 (acetate) | 4.53 | 4.63 | 4.55 | 4.62 |
| pH 6.8 (phosphate) | 6.85 | 6.87 | 6.87 | 6.88 |
| pH 8 (PBS) | 8.01 | 8.04 | 8.11 | 8.17 |
| NaOH (0.2M) | 11.97 | 11.98 | 11.87 | 11.91 |

TABLE 18

XRPD patterns observed in ethanol/hydrocarbon study

| | XRPD Pattern | |
|---|---|---|
| Solvent System | Amorphous input | Form A input |
| pH 1.2 (HCl—KCl) | HCl Salt Form | HCl Salt Form |
| pH 4.5 (acetate) | Form F | Form F |
| pH 6.8 (phosphate) | Form C | Form $H^A$ |
| pH 8 (PBS) | Form $H^B$ | Form $H^A$ |
| NaOH (0.2M) | Form C | Form $H^A$ and Form C |

What is claimed is:

1. A crystalline solid form of Compound 1:

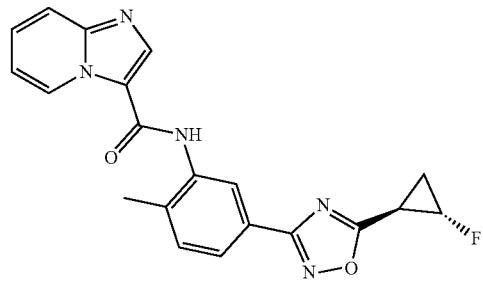

selected from Form C, characterized as having peaks in its X-ray powder diffraction pattern at about 10.1, about 12.5, about 15.2, about 19.7, about 20.9, about 23.0, and about 25.3 degrees 2-theta;

Form E, characterized as having peaks in its X-ray powder diffraction pattern at about 13.1, about 14.3, about 16.4, about 17.2, about 19.2, and about 24.5 degrees 2-theta;

Form G, characterized as having peaks in its X-ray powder diffraction pattern at about 5.8, about 12.3, about 16.8, about 17.0, about 17.5, about 22.6, and about 24.6 degrees 2-theta;

and Form H, characterized as having peaks in its X-ray powder diffraction pattern at about 12.9, about 13.2, about 14.1, about 17.9, about 24.6, about 25.4, and about 25.7 degrees 2-theta.

2. The crystalline solid form according to claim 1, having peaks in its X-ray powder diffraction pattern at about 10.1, about 12.5, about 15.2, about 19.7, about 20.9, about 23.0, and about 25.3 degrees 2-theta.

3. The crystalline solid form according to claim 2, having a DSC thermogram characterized by endothermic peaks at about 96° C. and about 171° C. and an exothermic peak at about 111° C.

4. The crystalline solid form according to claim 2, having an X-ray powder diffraction pattern substantially as shown in FIG. 1A.

5. The crystalline solid form according to claim 2, having a DSC thermogram substantially as shown in FIG. 1B.

6. The crystalline solid form according to claim 1, having peaks in its X-ray powder diffraction pattern at about 13.1, about 14.3, about 16.4, about 17.2, about 19.2, and about 24.5 degrees 2-theta.

7. The crystalline solid form according to claim 6, having a DSC thermogram characterized by an endothermic peak at about 63° C. and about 172° C.

8. The crystalline solid form according to claim 6, having an X-ray powder diffraction pattern substantially as shown in FIG. 3A.

9. The crystalline solid form according to claim 6, having a DSC thermogram substantially as shown in FIG. 3B.

10. The crystalline solid form according to claim 1, having peaks in its X-ray powder diffraction pattern at about 5.8, about 12.3, about 16.8, about 17.0, about 17.5, about 22.6, and about 24.6 degrees 2-theta.

11. The crystalline solid form according to claim 10, having a DSC thermogram characterized by an endothermic peak at about 109° C. and about 172° C. and an exothermic peak at about 118° C.

12. The crystalline solid form according to claim 10, having an X-ray powder diffraction pattern substantially as shown in FIG. 4A.

13. The crystalline solid form according to claim 10, having a DSC thermogram substantially as shown in FIG. 4B.

14. The crystalline solid form according to claim 1, having peaks in its X-ray powder diffraction pattern at about 12.9, about 13.2, about 14.1, about 17.9, about 24.6, about 25.4, and about 25.7 degrees 2-theta.

15. The crystalline solid form according to claim 14, having a DSC thermogram characterized by an endothermic peak at about 63° C. and about 173° C. and an exothermic peak at about 118° C.

16. The crystalline solid form according to claim 14, having an X-ray powder diffraction pattern substantially as shown in FIG. 5A.

17. The crystalline solid form according to claim 14, having a DSC thermogram substantially as shown in FIG. 5B.

18. A compound salt form: which is Compound 2:

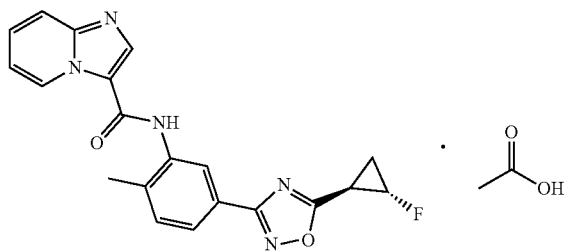

characterized as having peaks in its X-ray powder diffraction pattern at about 7.8, about 19.1, about 20.3, about 23.8, about 25.3, and about 27.0 degrees 2-theta.

19. The salt form according to claim 18, wherein said salt form is crystalline.

20. The salt form according to claim 18, having an XRPD substantially as shown in FIG. 6A.

21. A composition comprising a crystalline solid form according to claim 1 and a pharmaceutically acceptable carrier or excipient.

22. A method of inhibiting the activity of a c-kit kinase in a patient, comprising administering to said patient a crystalline solid form according to claim 1, or a composition thereof.

23. A composition comprising the salt form according to claim 18 and a pharmaceutically acceptable carrier or excipient.

24. A method of inhibiting the activity of a c-kit kinase in a patient, comprising administering to said patient a crystalline solid form according to claim 18, or a composition thereof.

* * * * *